(12) United States Patent
Sanders et al.

(10) Patent No.: US 6,277,891 B1
(45) Date of Patent: Aug. 21, 2001

(54) NITRIC OXIDE INHIBITS RHINOVIRUS INFECTION

(75) Inventors: Scherer P. Sanders, Lutherville; David Proud, Baltimore, both of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/113,310

(22) Filed: Jul. 10, 1998

Related U.S. Application Data

(60) Provisional application No. 60/052,307, filed on Jul. 11, 1997.

(51) Int. Cl.[7] ........................ A61K 31/04; A61K 31/045; A61K 31/13
(52) U.S. Cl. ....................... 514/742; 514/724; 514/668
(58) Field of Search ................................ 514/742, 724, 514/668

(56) References Cited

U.S. PATENT DOCUMENTS 5,455,279  10/1995  Lipton .................................. 514/742

OTHER PUBLICATIONS

Croen 119CA:115219, 1993.*

Karupiah et al 119 CA: 201499, 1993.*

Mannick et al 125 CA: 25680, 1996.*

Scherer P. Sanders et al. "Nitric Oxide Inhibits Rhinovirus–Induced Cytokine Production and Viral Replication in a Human Respiratory Epithelial Cell Lines" Journal of Virology, Feb. 1998 pp 934–942.

* cited by examiner

Primary Examiner—Russell Travers
(74) Attorney, Agent, or Firm—Banner & Witcoff

(57) ABSTRACT

Nitric oxide generating compounds or compounds which induce in situ synthesis of nitric oxide can be used to inhibit rhinovirus infection. Nitric oxide has the ability to inhibit both viral replication as well as the synthesis of cytokines, in particular the proinflammatory cytokines. Thus the symptoms of rhinovirus infections can be ameliorated by treatments to increase nitric oxide in the respiratory tract.

22 Claims, 16 Drawing Sheets

NITRIC OXIDE INHIBITS RHINOVIRUS INFECTION

This application claims the benefit of application Ser. No. 60/052,307 filed Jul. 11, 1997.

This invention was made using support from the U.S. government, under National institutes of Health grant AI37163. Therefore the government retains certain rights in the invention.

TECHNICAL FIELD OF THE INVENTION

This invention is related to the field of virology. More particularly it relates to the field of human rhinoviruses.

BACKGROUND OF THE INVENTION

Rhinovirus infections are the predominant cause of the common cold (18), the most frequently experienced acute respiratory illness in humans. Recent evidence also implicates rhinovirus infections as an important precipitating factor for exacerbations of asthma (21, 22, 37), chronic bronchitis (35), sinusitis (19, 50), and otitis media (3). Despite the high health care costs associated with rhinovirus infections, the underlying process by which viral infection leads to symptomatology is poorly understood.

The epithelial cell is the primary site of rhinovirus infection (6, 51). In contrast to other respiratory viruses, such as influenza, cytotoxic damage of infected epithelial cells does not appear to play a role in the pathogenesis of rhinovirus infections, since cytotoxicity is not observed either in infected human epithelial cell cultures (49) or in the nasal mucosa of infected individuals (53, 54). In light of this, emphasis has focused on the concept that symptoms may result from the actions of proinflammatory mediators that are generated as a consequence of rhinovirus infection. Support for this hypothesis has come from two lines of evidence: 1) Studies of subjects with experimentally-induced, or naturally-acquired colds have demonstrated increased levels of several mediators, including kinins (36, 41), IL-1 (40), and IL-6 (55) in nasal secretions during symptomatic rhinovirus infections, and 2) infection of purified human respiratory epithelial cell populations with rhinovirus has been shown to induce production of proinflammatory cytokines, including IL-8, IL-6 and GM-CSF (49, 55), that could contribute to disease pathogenesis. To date, however, the specific biochemical events involved in the production of each of these cytokines by rhinoviruses are incompletely understood, and the role of specific cytokines, and other mediators, in the pathogenesis of colds remains to be established.

SUMMARY OF THE INVENTION

It is an object of the present invention to provide methods of alleviating symptoms induced by a rhinoviral infection.

It is another object of the present invention to provide methods of reducing rhinoviral replication.

It is an object of the present invention to provide methods of reducing cytokine production induced by a rhinovirus.

It is still another object of the invention to provide a method for screening to compounds to identify candidate therapeutic or prophylactic agents for rhinoviral infection.

These and other objects of the invention are achieved by providing a method of alleviating symptoms induced by a rhinoviral infection which comprises administering a compound to a human infected with a rhinovirus. The compound releases nitric oxide (NO). An amount is administered which is sufficient to alleviate one or more symptoms associated with the infection.

According to another aspect of the invention a method is provided of reducing rhinoviral replication. The method comprises contacting human respiratory epithelial cells which are infected by a rhinovirus with a compound. The compound is one which releases NO. Sufficient compound is administered to inhibit replication of the rhinovirus.

According to yet another aspect of the invention a method is provided of reducing cytokine production induced by a rhinovirus. The method comprises the step of contacting human respiratory epithelial cells which are infected by a rhinovirus with a compound. The compound is one which releases NO. Sufficient compound is administered to inhibit cytokine production induced by the rhinovirus.

Another embodiment of the invention is a method of alleviating symptoms induced by a rhinoviral infection. The method comprises administering an effective amount of a compound to a human infected with a rhinovirus. The compound induces nitric oxide synthase (NOS) in human respiratory epithelial cells, whereby the symptoms of the infection are alleviated.

Still another embodiment of the invention is provided by a method of reducing rhinoviral replication. The method comprises contacting human respiratory epithelial cells which are infected by a rhinovirus with a compound. The compound induces NOS in the human respiratory epithelial cells. The compound is administered in an amount effective to inhibit replication of the rhinovirus.

Even another aspect of the invention is a method of reducing cytokine production induced by a rhinovirus. The method comprises contacting human respiratory epithelial cells which are infected by a rhinovirus with a compound. The compound is one which induces NOS in the human respiratory epithelial cells. An amount is administered which is effective to inhibit cytokine production induced by the rhinovirus.

Yet another embodiment of the invention is a method for testing compounds to identify candidate agents for therapeutic or prophylactic treatment of a common cold or other disease associated with human rhinoviruses. The method comprises the step of infecting human respiratory epithelial cells with a human rhinovirus; contacting the cells with a test compound; and measuring the amount of at least one proinflammatory or eosinophil-active cytokine produced by the respiratory epithelial cells, wherein a test compound which reduces the amount of the cytokine produced is a candidate agent for prophylactic or therapeutic treatment of human rhinovirus infection.

Another aspect of the invention is another method for testing compounds to identify candidate agents for therapeutic or prophylactic treatment of a common cold or other disease associated with human rhinoviruses. The method comprises the steps of: infecting human respiratory epithelial cells with a human rhinovirus; contacting the cells with a test compound; and measuring the amount rhinoviral genome replicated in the respiratory epithelial cells, wherein a test compound which reduces the amount of the rhinoviral genome replicated is a candidate therapeutic or prophylactic agent for prophylactic or therapeutic treatment of human rhinovirus infection.

According to another aspect of the invention a pharmaceutical composition for treating rhinovirus infections is provided. The composition comprises a liquid formulation comprising a compound which releases NO. The liquid formulation is nose drops.

Another embodiment of the invention is a nose spray- or dropper-bottle for administering a pharmaceutical composition to a human nose. The bottle comprises a liquid formulation comprising a compound which releases NO.

Still another aspect of the invention is an inhaler or nebulizer for delivering an antirhinoviral composition to the respiratory tract of a human. The device comprises a liquid formulation comprising a compound which releases NO.

The invention thus provides the art with compositions, devices, and methods for treating rhinovirus infections as well as methods for identifying additional candidate therapeutic and prophylactic agents.

BRIEF DESCRIPTION OF THE DRAWINGS

FIG. 1: Cytokine production from BEAS-2B cells 24 h after infection with each of several strain of human rhinovirus (HRV). Data represent mean ±SEM from 3 experiments. FIG. 1A shows production of IL-8, while

FIG. 2: Time course of induction of steady state mRNA levels and protein for IL-8 (Left) and IL-6 (Right) from HRV-14 infected BEAS-2B cells. FIGS. 2C and 2D show densitometric ratios, while

FIG. 4: Cycloheximide does not alter stead state mRNA levels for IL-8 (Left) and IL-6 (Right) measured 1 h after infection with HRV-16. The FIGS. 4A and 4B show a representative Northern blot, while

FIG. 5: Effects of Budesonide ($10^{-7}$M) on steady state mRNA levels and protein for IL-8 (Left) and IL-6 (Right) from HRV-16 infected BEAS-2B cells.

FIG. 6: Dose-dependent inhibition of cytokine production from HRV-16 infected BEAS-2B cells by NONOate. FIG. 6A shows mean ±SEM values from 4 experiments for IL-8 production at 4 h and at 24 h after HRV-16 infection, while

FIG. 8: Comparison of the effects of inactive NONOate, and of active NONOate added at differing times during the infection procedure, on HRV-16 induced cytokine production from BEAS-2B cells. NONOate was used at a final concentration of 1000 $\mu$M, and protein levels were measured 4 h after infection.

DETAILED DESCRIPTION

Figure 1A:
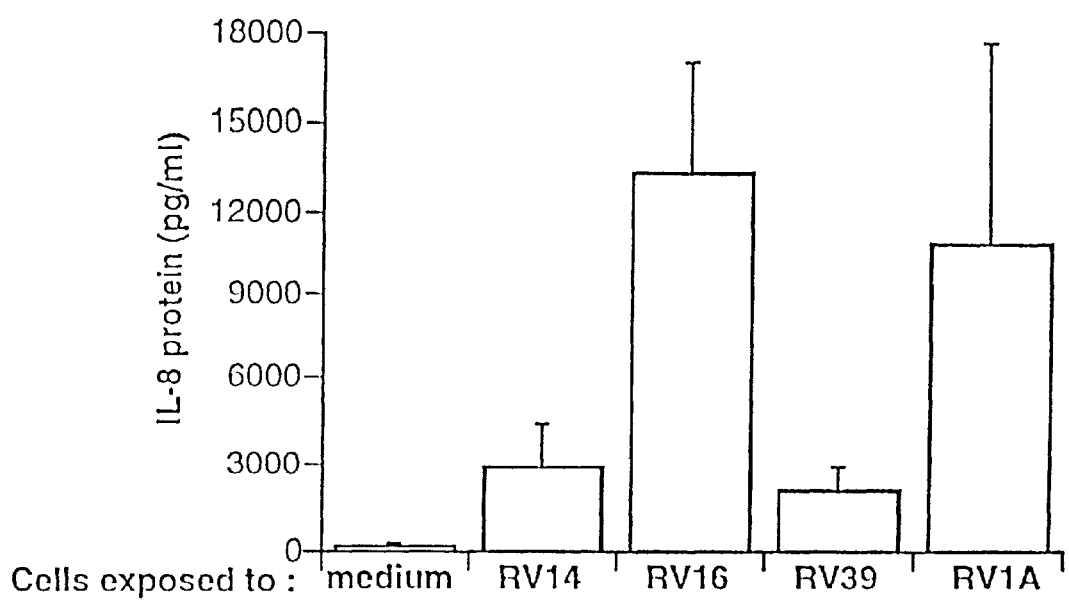

We have discovered that human rhinoviruses induce production of proinflammatory cytokines from human respiratory epithelial cells. Moreover, we have found that nitric oxide markedly inhibits rhinovirus replication and virally induced cytokine expression without affecting mRNA levels for the cytokines. Administration of NO donors or nitric oxide synthase (NOS) inducers can be used, therefore, to achieve prophylactic and therapeutic goals. Since replication and inflammation are affected by NO, such treatments lead to a shorter duration of infection as well as reduced symptoms.

Preferably, amounts of NO donors or NOS inducers are administered to achieve a significant inhibition of symptoms, proinflammatory cytokine synthesis, eosinophil-active cytokine synthesis, and/or viral replication. Such inhibition is at least 10%, preferably at least 20%, and increasingly more preferably at least 30%, 40%, 50%, 60%, 70%, 80%, 95%, or 99%. Symptoms which are often abated with human rhinoviruses include the common cold, asthma, sinusitis, otitis media, and bronchitis. Any of these or other symptoms may be alleviated or inhibited according to the present invention.

Methods of treating according to the present invention include any method by which the active compounds can gain access to the human respiratory epithelial cells. Such methods include without limitation: topical, by nose drops, by an inhalant, via an aerosol, by a spray, by a gargle or wash.

Compounds which generate NO in situ can be used. Such compounds include without limitation nitroglycerin, organic nitrates, linsidomine, molsidomine, and N-acetylpenicillamine, 3-morpholinosyndonimine (SIN-1), No-releasing aspirine derivatives, NOC-18, sodium niroprusside, GEA 3162, GEA3175, GEA5171, nicorandil, C87 3754, N)-naroxen, S-nitrosogsteine, S-nitrosoglutathione, FR 144420 and FK409, NOR4, NOC-7, [N(O)NO]-polymers, pirsidomine, 2,2-diethyl-1-nitrexylhydrazine, furoxans. Preferably the compounds comprise a $N_2O_2^-$ moiety. More preferably the compound is 3-2-hydroxy-2-nitroso-1-propylhydrazino)-1-propanamine (a member of the class of NONOates). Such compounds have been known for topical application to heart tissue in both pastes and patches. These compounds can be applied to the nose, mouth, throat, bronchi or any portion of the respiratory system. Intravenous administration as well as direct pharmacologic injection may also be used. Suitable dosages will generally be from about 0.01 mg to about 10 mg per application, preferably from 0.1 mg to 5 mg, and more preferably from 1–3 mg.

Compounds which can be used as NOS inducers include any which are known in the art. These include without limitation interferon γ, TNF-α, IL-1β, and bacterial lipopolysaccharide.

Devices for delivering the compositions and compounds to the respiratory tract or ear according to the methods of the present invention may be any which are conventionally used in the art for such purposes. These include inhalers, nebulizers, nose drop bottles, dropper bottles. Any formulation which is suitable for delivering to the nose, mouth, throat, bronchia, lungs, ears, and/or sinuses.

The above disclosure generally describes the present invention. A more complete understanding can be obtained by reference to the following specific examples which are provided herein for purposes of illustration only, and are not intended to limit the scope of the invention.

EXAMPLES

The current studies were undertaken to further delineate the kinetics and mechanisms of rhinovirus induced cytokine generation by epithelial cells, and to evaluate the effects of potential therapeutic interventions on these pathways. We have focused on viral production of IL-8 and IL-6 because these cytokines are produced in relatively large amounts upon rhinovirus infection, and because they have biological properties that are of interest with respect to the pathogenesis of colds. IL-8 is a potent chemoattractant for, and activator of; neutrophils (5) and also has chemotactic activity for lymphocytes (28), the two predominant cell types in the nasal mucosa during rhinovirus infections (29, 54). IL-6 is not only capable of stimulating T cell activation, inducing B cell differentiation and antibody production (1), but can also stimulate mucosal IgA immune responses (42). In terms of potential interventions, we have used two approaches. Based upon the wide ranging immunomodulatory and anti-inflammatory effects of glucocorticoids (44), including their ability to inhibit the production of several cytokines in a variety of cell types (45), we examined the effects of the potent glucocorticoid, budesonide, on rhinovirus infection in epithelial cells. As a novel alternative approach, we also investigated the ability of a nitric oxide donor to inhibit viral replication and virally-induced cytokine production in epithelial cells. Studies have demonstrated that the vasodilator nitric oxide (NO) can exert modulatory effects on inflammation (39), and nitric oxide has been shown to have antiviral effects in some animal models (7, 12, 20, 24, 32), but this property has not been examined in human respiratory epithelial cells. Our studies show that budesonide modestly inhibits rhinovirus-induced cytokine generation without affecting viral replication. By contrast, NO markedly inhibits rhinovirus-induced cytokine generation as well as viral replication and may play a therapeutic role in rhinovirus infections.

Example 1

Effects of cell passage: Preliminary studies indicated that there was a marked effect of repeated cell passage on cytokine production from BEAS-2B cells. Although data obtained were always qualitatively identical for each passage, there was a progressive effect of cell passage on absolute levels of cytokines produced. For example, in four experiments performed used an identical protocol with consecutive cell passages, production of IL-8 decreased from 7690 pg/ml to 3090 pg/ml. For this reason, each type of experiment performed below was always carried out in matched experiments using the same cell passages.

Figure 10A:
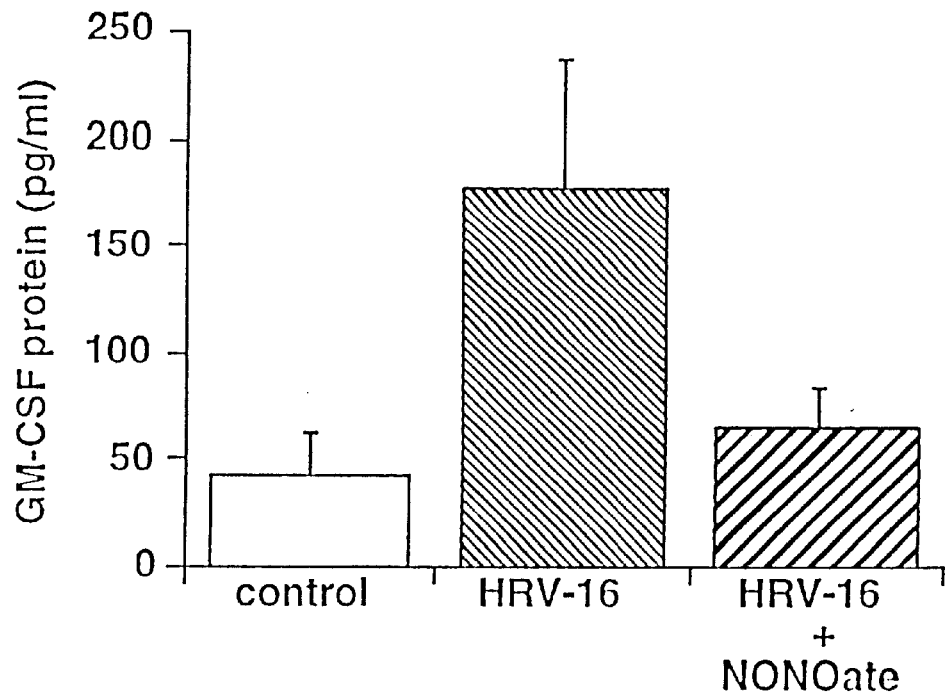
FIG. 10. Effects of NONOate (500 $\mu$M) on production of GM-CSF (left) and RANTES (right) from BEAS-2B cells 24 hours after infection with HRV-16. The data represent means ±SEM of values from 4 experiments.
Figure 10B:
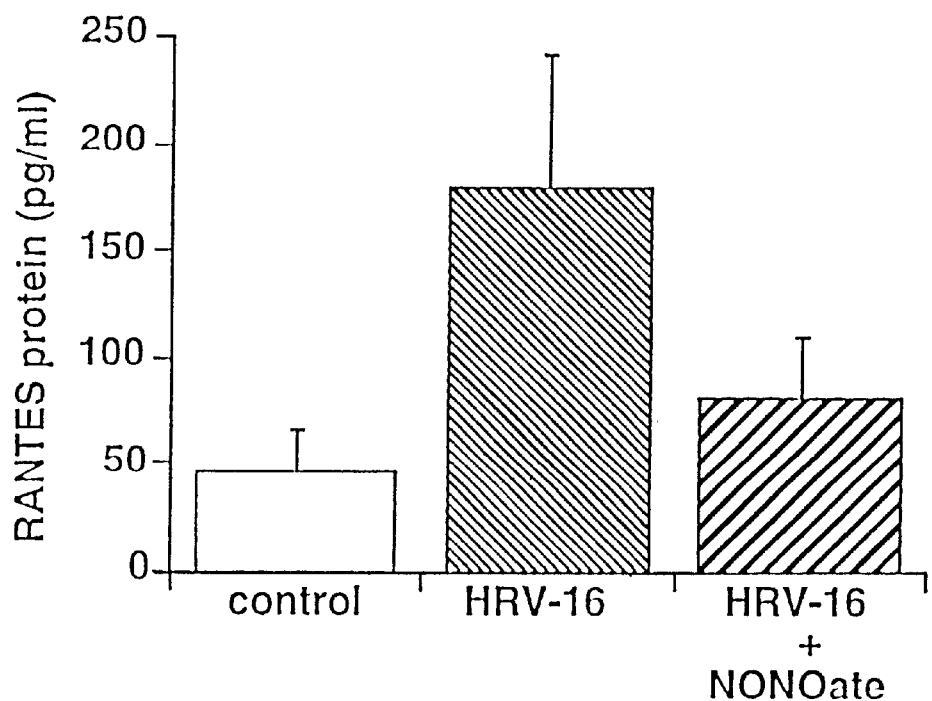

Comparison of effects of several rhinovirus strains on cytokine production from BEAS-2B cells. The effects on cytokine production of equal infective doses of four different strains of rhinovirus were compared in cultures of BEAS-2B cells. Three of the strains used, types 14, 16, and 39, are members of the major group of rhinoviruses that use intercellular adhesion molecule-1 (ICAM-1) as their receptor, while type 1A is a member of the ICAM-1-independent minor group. All of the strains induced IL-8 and IL-6 production measured at 24 h following infection (FIG. 10). With all viral strains generated levels of IL-8 were approximately 10 fold higher than IL-6.

Materials: The following reagents were purchased: Dulbecco's Minimal Essential Medium (DMEM) Eagle's Minimal Essential Medium (EMEM), Ham's F-12 medium, HBSS, L-glutamine, penicillin/streptomycin/fungizone, trace elements, and retinoic acid (Biofluids, Rockville, Md.); hydrocortisone, epithelial cell growth factor and endothelial cell growth supplement, (Collaborative Research, Bedford, Mass.); fetal bovine serum (Gemini Bio Products, Inc., Calabasa, Calif.); transferrin and insulin (GIBCO BRL, Grand Island, N.Y.); 3-(2-hydroxy-2-nitroso-1-propylhydrazino)-1-propanamine (NONOate) from Cayman Chemical Company (Ann Arbor, Mich.); RNAzol™B (Tel-Test, Inc., Friendswood, Tex.); agarose (FMC Bioproducts, Rockland, Me.), Mops (Boehringer Mannheim, Indianapolis, Ind.), and $\alpha^{32}$P-dCTP (Amersham, Arlington Heights, Ill.). All other chemicals were purchased from Sigma Chemical Company (St. Louis, Mo.). Budesonide was generously provided by Drs. Per Andersson and Ralph Brattsand (Astra Pharmaceutical Production, Lund, Sweden).

The following stock buffers were employed: 10×Mops (0.2 M Mops, 0.05 M sodium acetate, 0.01 M EDTA); 50×Denhardt's (1% ficoll, 1% polyvinylpyrrolidine, 1% bovine serum albumin); and 20×SSPE (175.3 g NaCl, 27.6 g $NaH_2PO_4.H_2O$, 7.4 g EDTA in 1 liter $H_2O$, pH 7.4).

Viruses and Cell Lines: Human rhinovirus types 14 (HRV-14), 16 (HRV-16 ), 39 (HRV-39) and 1A (HRV-1A), WI-38 cells and HeLa cells were purchased from American Type Culture Collection (Rockville, Md.). Additional viral stocks for HRV-14 and HRV-16 were generated by passage in HeLa or WI-38 cells, respectively, as previously described (49). It was not possible to generate equivalent stocks of these two viral strains using the same host cell line, since the two strains displayed marked preferences in terms of capacity to infect and replicate in these cell lines. This variable sensitivity of host cells to different strains of rhinovirus has been documented previously (11). For some experiments, HRV-16 was purified to remove ribosomes and soluble factors of WI-38 origin by centrifugation trough sucrose, according to published methods (16). Inactivation of HRV-16 was performed by UV exposure for 30 min as previously described (49). For experiments using HRV-39 and 1A, viral stocks were used directly as obtained from the supplier. The HRV-39 stock provided had been prepared in WI-38 cells, while the HRV-1A stock obtained was generated in HeLa cells. The BEAS-2B cell line (43) was generously provided by Dr. Curtis Harris (National Cancer Institute, Bethesda, Md.).

Epithelial Cell Culture: Primary human tracheal epithelial cells were obtained by protease digestion of human tissue as previously described (10). Both primary cells and BEAS-2B cells were grown in culture medium consisting of Ham's F-12 nutrient medium with penicillin (100 U/ml), streptomycin (100 U/ml), fungizone (250 ng/ml), L-glutamine (2 mM), phosphoethanolamine/ethanolamine (0.5 mM), transferrin (10 $\mu$g/ml), endothelial cell growth supplement (3.75 $\mu$g/ml), epidermal growth factor (12.5 $\mu$ng/ml), insulin (5 $\mu$g/ml), hydrocortisone ($10^{-7}$ M), cholera toxin (10 ng/ml), 3,3',5-triodothyronine ($3\times10^{-9}$ M), retinoic acid (0.1 ng/ml), and trace elements.

This medium is hereafter referred to as F12/10x. The cells were incubated at 37° C. in 95% air and 5% $CO_2$. For the experiments, cells between passages 35 and 50 were plated on 6-well plates or 75 $cm^2$ flasks (Costar, Cambridge, Mass.) at a density of $2.5\times10^4$ cells/$cm^2$.

Viral Infection of BEAS-2B cells: Monolayers of BEAS-2B cells (70–80% confluent) were washed 3 times with HBSS. Rhinovirus (strain 14, 16, 39, or 1A) was added to the cells at a concentration of $10^4$ $TCID_{50}$ units/ml HBSS. This equates to an infectious dose of 0.001$TCID_{50}$ units/BEAS-2B cell, although it is unclear what this represents in terms of multiplicity of infection (MOI—infectious units per cell) for BEAS-2B cell, since the capacity of rhinovirus to infect different host cells is quite variable (see above). The cells were incubated with the virus at 34° C. for 1 h, washed 3 times with F12/10x, and then fresh F12/10x medium was added to the cells. Supernatants were removed from the cells at various times after infection and stored at –80° C. for later analysis of cytokine protein production and viral content. In some experiments, total cellular RNA was extracted from the cells at various times after infection and stored at –80° C. for later analysis.

Quantification of IL-8 and IL-6: Levels of cytokines m cell supernatants were determined using specific ELISAs. Measurements of IL-8 were performed using a previously described ELISA sensitive to 30 pg/ml of cytokine (49), while levels of IL-6 were assayed using a commercial kit sensitive to 15 pg of IL-6 /ml (Biosource International, Camarillo, Calif.). Neither the culture medium, nor vehicles for drugs used in our experiments caused any nonspecfic interference effects in either assay.

Statistical Analysis: Data are expressed as the mean ±SEM. Comparisons of the kinetics of RNA expression, protein secretion, and viral titers were performed using a one-way ANOVA The effects of cycloheximide and glucocorticoid on RNA expression and protein secretion were compared using the Student's t-test for paired samples. Comparisons of the effects of NONOate on cytokine production, viral titers, and RNA expression were made by two-way ANOVA with one repeated measure, except for the experiments comparing active and inactive NONOate that were analyzed by a one-way ANOVA When significant variance ratios were obtained, pair-wise comparisons of the means were performed with the Least Significant Difference Multiple-range Test (47). Differences were considered significant for values of $p<0.05$.

Example 2

Figure 1B:
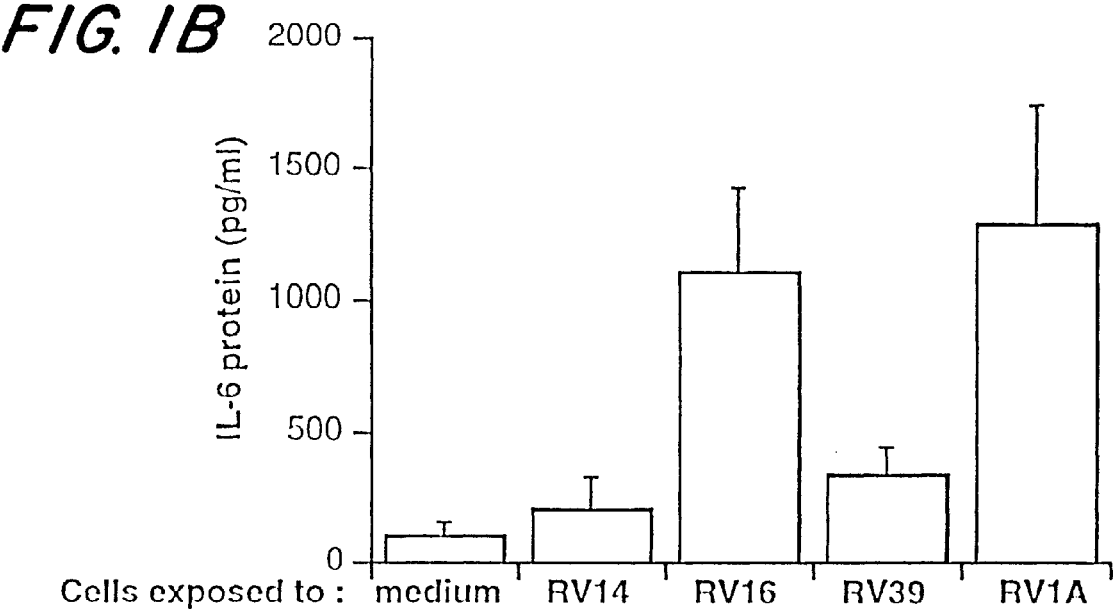
FIG. 1B shows production of IL6.
Figure 2A:
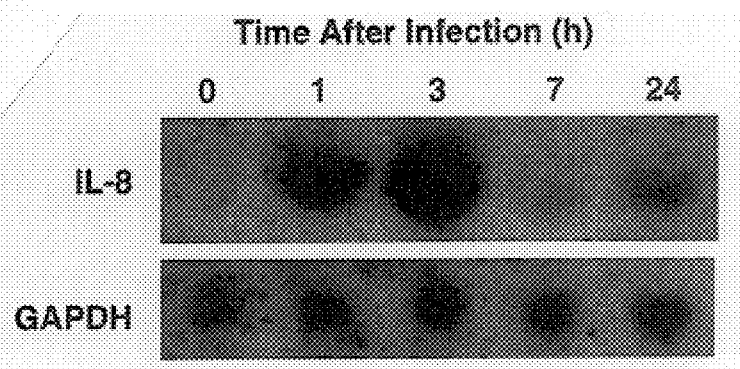
FIGS. 2A and 2B show Northern blots for each cytokine and for the housekeeping gene, GAPDH.
Figure 2C:
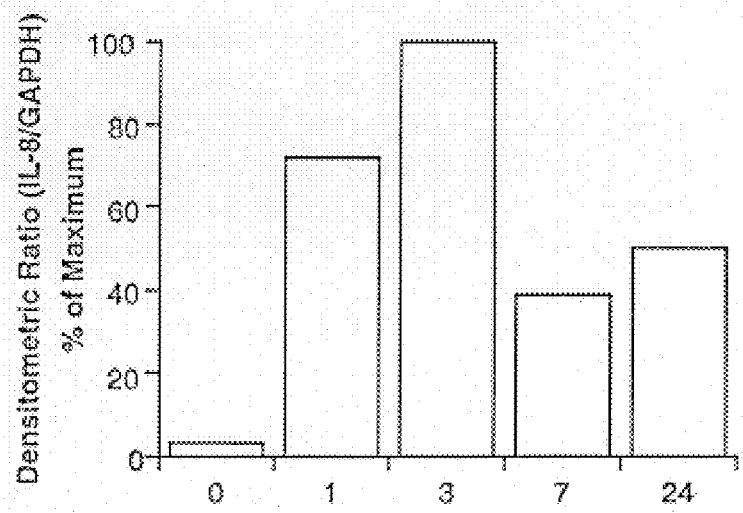
Figure 2E:
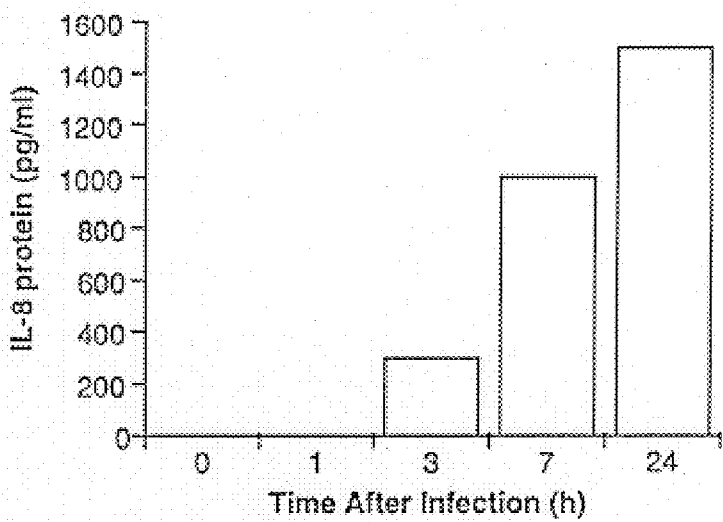
FIGS. 2E and 2F show protein levels produced at each of the time points noted. Data are from a representative experiment (n=3).
Figure 2B:
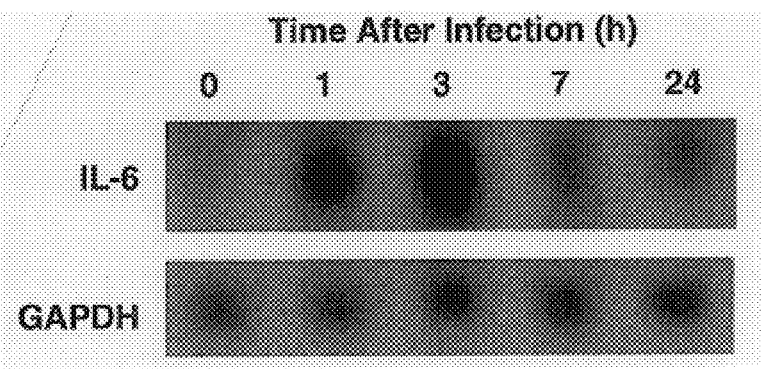
Figure 2D:
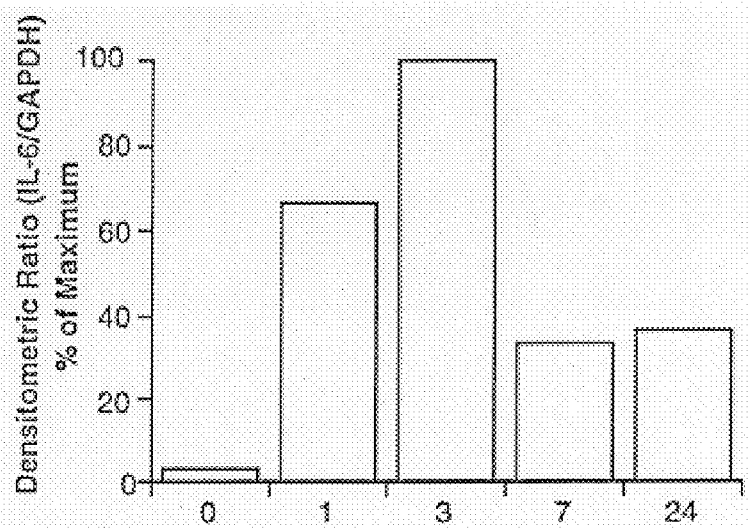
Figure 2F:
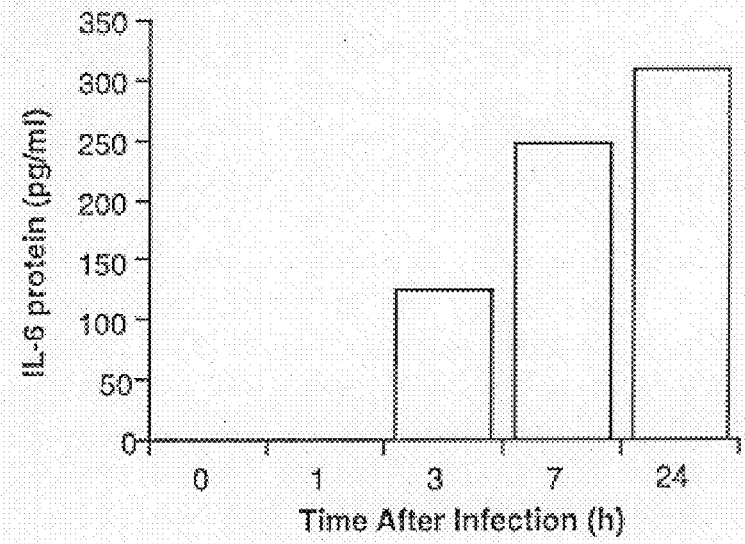
Figure 3A:
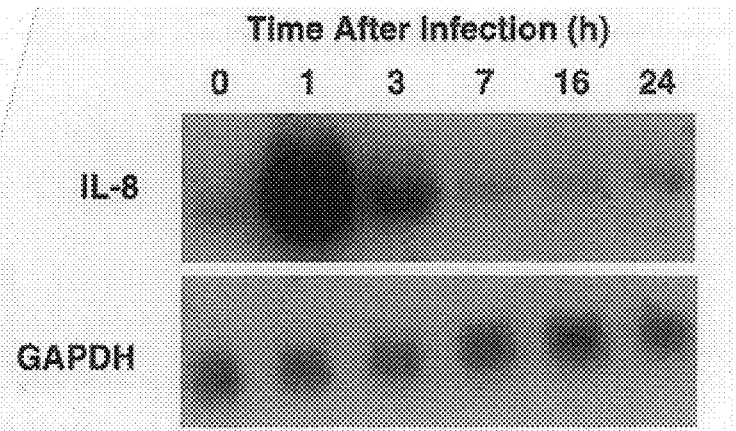
FIGS. 3A and b show representative Northern blots for each cytokine and for the housekeeping gene, GAPDH.
Figure 3C:
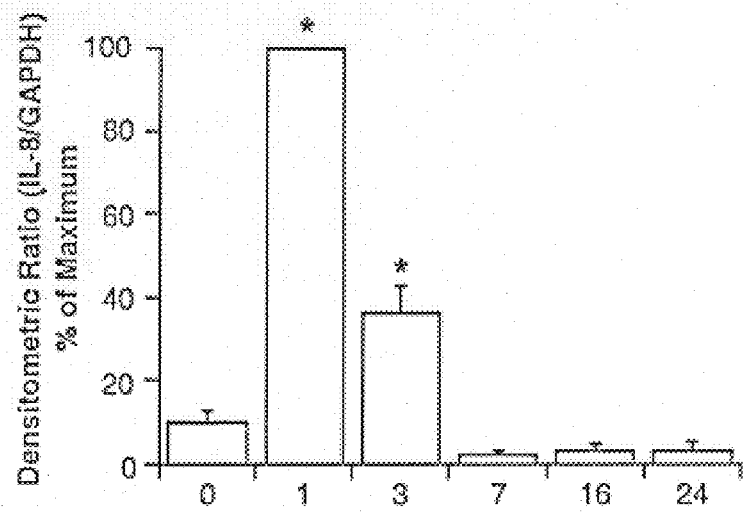
FIGS. 3C and 3D show the mean ±SEM values of densitometric ratios for 4 experiments.
Figure 3E:
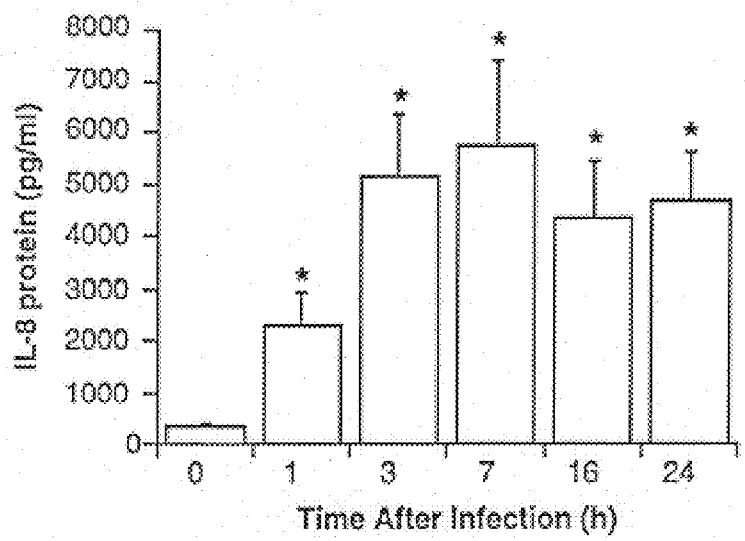
FIGS. 3E and 3F show the means plus SEM values of protein produced for 4 experiments at each time point. Asterisks indicate significant increases in each parameter relative to the zero time control ($p<0.05$ in each case).
Figure 3B:
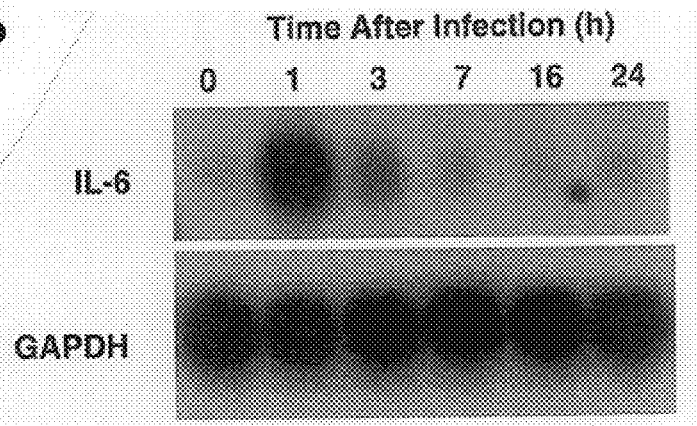
FIG. 3: Tune course of induction of steady state mRNA levels and protein for IL-8 (Left) and IL-6 (Right) from HRV-16 infected BEAS-2B cells.
Figure 3D:
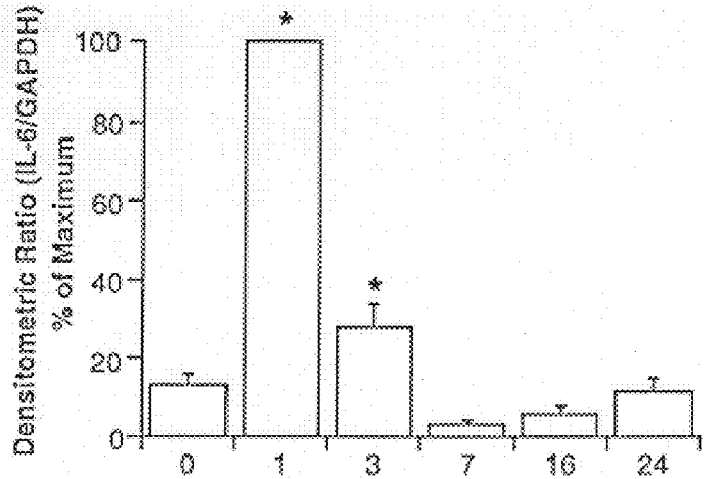
Figure 3F:
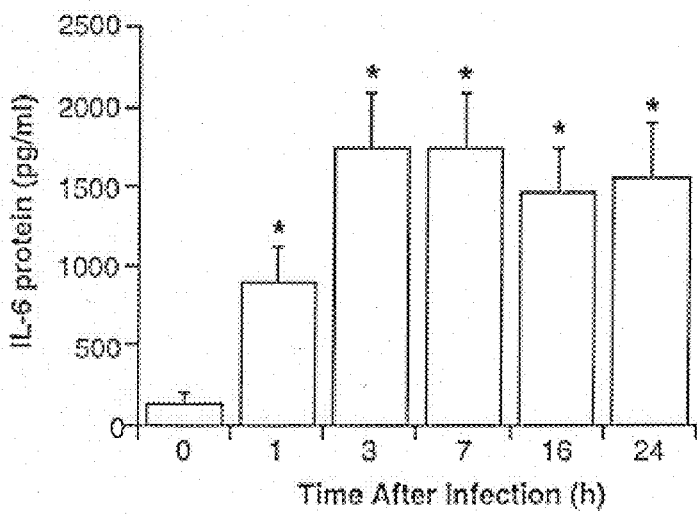
Figure 4A:
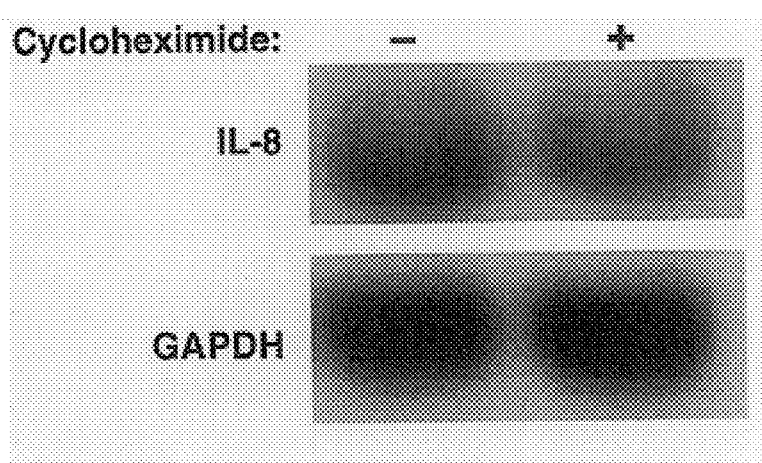
Figure 4C:
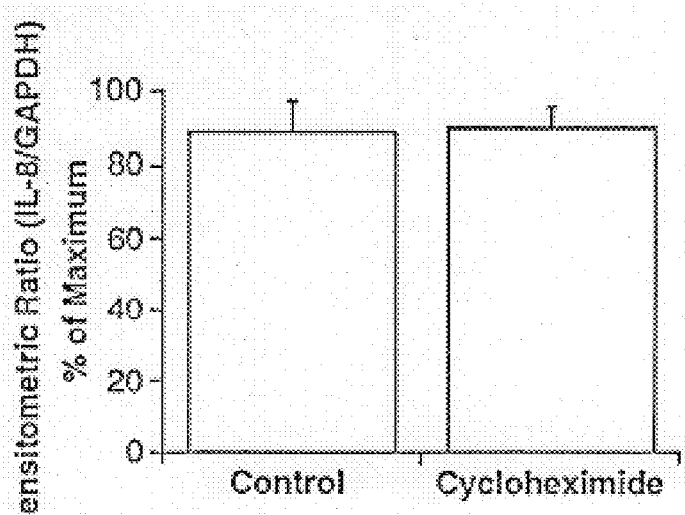
FIGS. 4C and 4D show the mean ±SEM values of densitometric ratios for 4 experiments.
Figure 4B:
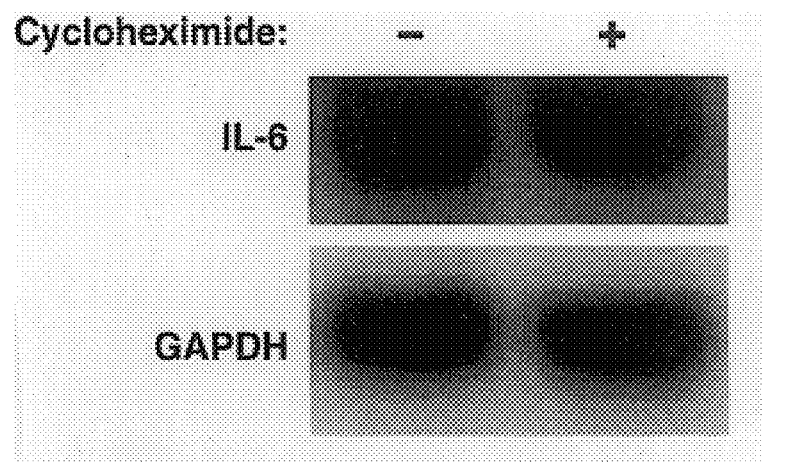
Figure 4D:
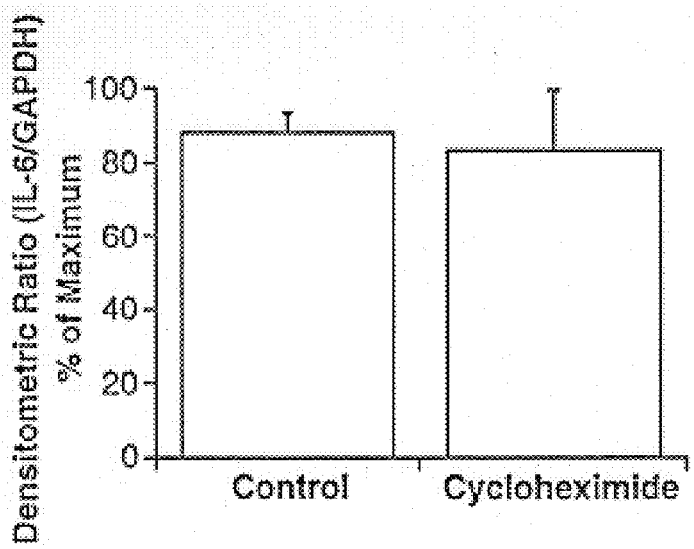
Figure 5A:
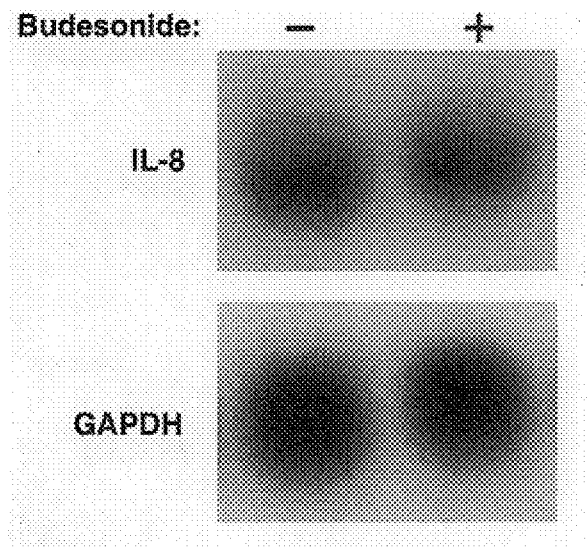
FIGS. 5A and 5B show representative Northern blots using mRNA extracted 1 h after infection.
Figure 5C:
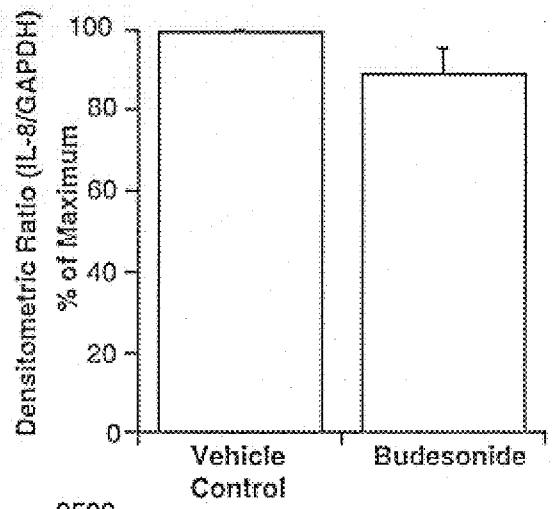
FIGS. 5C and 5D show the mean ±SEM values of densitometric ratios from 3 experiments.
Figure 5E:
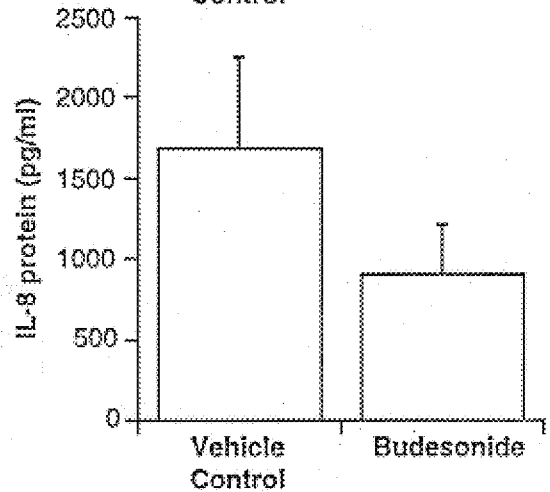
FIGS. 5E and 5F show the mean ±SEM values of protein produced 7 h after infection in 3 experiments.
Figure 5B:
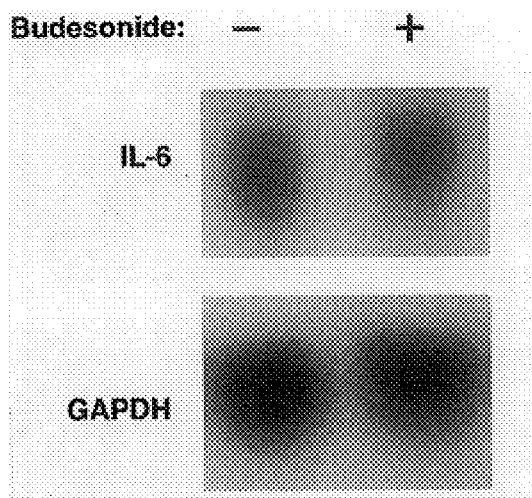
Figure 5D:
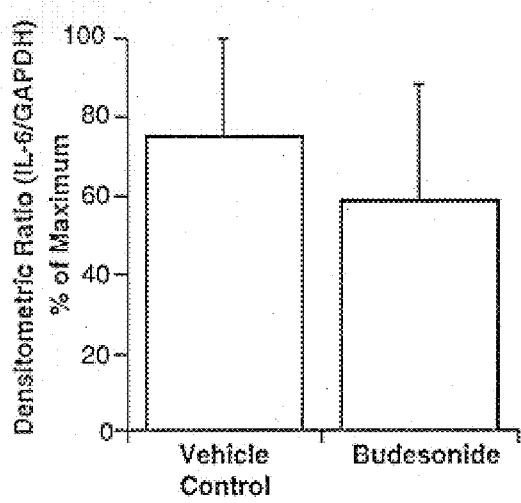
Figure 5F:
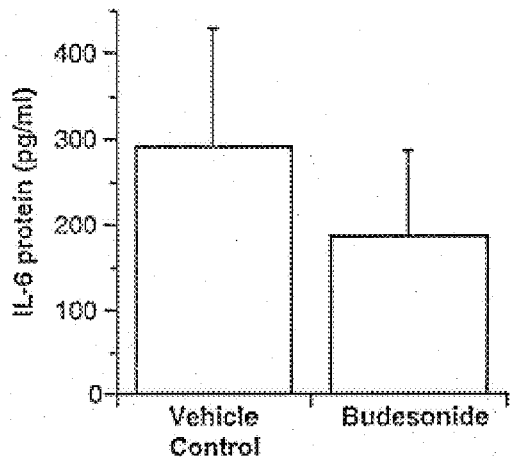

Kinetics of cytokine mRNA expression and protein secretion: FIG. 2 demonstrates that mRNA for IL-8 and IL-6 were significantly elevated within one hour post HRV-14 infection. Maximal expression occurred by 3 h but mRNA levels were still higher than noninfected controls at 24 h post-infection. Induction of mRNA was followed by significant elevations in IL-8 and IL-6 proteins in the supernatants. Increased cytokine production occurred by 3 h post-infection, and reached maximal concentrations by 24 h. Interestingly, the time course of IL-8 and IL-6 production after HRV-16 infection was more rapid than that observed for HRV-14 (FIG. 3). Maximal mRNA expression occurred within 1 h post-infection and maximal protein production occurred within 7 h. Consistent with the data shown above (FIG. 1), the magnitude of cytokine generation was about 4-fold greater following HRV-16 infection than the response following HRV-14 infection (FIG. 3 vs FIG. 2). Because HRV-16 produced a more rapid and robust production of cytokines, and is the strain that will be used for later in vivo studies, subsequent experiments on the mechanism of induced cytokine generation were performed using HRV-16. To confirm the specificity of HRV-16 effects, three matched experiments were performed comparing IL-8 generation by active and UV-inactivated viral preparations. Active virus generated 3307±1156 pg/ml of IL-8 while UV inactivated virus produced only 520±90 pg/ml (control, noninfected cells produced 345±110 pg/ml). Specificity was further confirmed by demonstrating that similar amounts of IL-8 were generated, in matched experiments, when cells were infected with our standard viral preparation or with an equal infective dose of the same stock of HRV-16 purified by sucrose density centrifugation (2080±340 pg/ml and 1750±500 pg/ml, respectively; n=3). The time course of viral induction of IL-8 and IL-6 was also identical for the standard and purified preparations of HRV-16 (not shown).

Example 3

Viral titers post HRV-16 infection: Supernatants were collected at various times post-infection and assessed for viral titers in the WI-38 cell cytotoxicity assay for HRV-16. Virus was detected in the culture medium beginning approximately 7 h following infection and progressively increased between 7 and 24 h after infection (Table 1). Supernatants collected during a second 24 h period after infection contained levels of virus similar to those seen after 24 h (see Table 2 below). This pattern of viral titers is ally identical to that previously observed with HRV-14 (49).

TABLE 1

Viral Content of Supernatants from BEAS-2B cells at Differing Times after Infection with Human Rhinovirus-16

| Time Post Infection (hours) | Viral Titer (Log $TCID_{50}$ units)* |
|---|---|
| 0 | ND |
| 1 | ND |
| 3 | ND |
| 7 | 1.25 ± 0.25 |
| 16 | 2.25 ± 0.25 |
| 24 | 2.4 ± 0.13 |

*Data represent mean ± SEM from 4 experiments

TABLE 2

Effects of NONOate on Viral Titers Decreases with Time

| Treatment | Viral Titers (Log TCID$_{50}$ units)* | |
|---|---|---|
| | 0–24 h | 24–48 h |
| HRV-16 | 2.8 ± 0.1 | 2.9 ± 0.1 |
| HRV-16 + 300 μM NONOate | 2.5 ± 0.3 | 2.8 ± 0.1 |
| HRV-16 + 1000 μM NONOAte | 0.5 ± 0.5‡ | 2.4 ± 0.2 |

*Data represent mean ± SEM from 3 experiments.
‡p < 0.05 vs. HRV-16 alone

Example 4

Effects of cycloheximide on IL-8 and IL-6 mRNA expression: Levels of mRNA for IL-8 and from HRV-16 infected cells treated with cycloheximide (10 μg/ml) were not different from control infected cells (FIG. 4). Comparisons were made at 1 h after viral infection, the time of peak mRNA expression in the kinetics studies described above.

Effect of Cycloheximide on HRV-16 -induced IL-8 and IL-6 mRNA expression: BEAS-2B cells were treated with cycloheximide (10 μg/ml), or medium control, for 1 h before viral infection. The drug was aso present during, and after, infection with HRV-16 . At 1 h post infection, RNA was harvested for Northern analysis. This concentration of cycloheximide was used because it has previously been shown to inhibit TNFa and IFNg-induced expression of RANTES mRNA in this cell line (48).

Example 5

Effect of glucocorticoid pretreatment on cytokine production and viral titers: Cells were treated with $10^{-7}$ M budesonide or vehicle control for 24 h prior to viral infection. Comparisons of RNA expression and protein production were made at the times of maximal response as determined in the kinetics experiments described above; one hour for mRNA and 7 h for cytokine protein production. IL-8 and IL-6 mRNA expression in HRV-16 infected BEAS-2B cells was not significantly altered by budesonide (FIG. 5). In every experiment, however, the production of IL-8 and IL-6 proteins from budesonide-treated BEAS-2B cells was lower than from control infected cells (P<0.05 for paired comparison of normalized data). Viral titers (2.2 ±0.6 log TCID$_{50}$ units) were not altered by budesonide exposure.

Effect of budesonide on cytokine production and viral replication: Budesonide was prepared as a $10^{-2}$ M stock solution in DMSO. Since the BEAS-2B cells are usually maintained in growth medium containing low levels of hydrocortisone, the cells for these experiments were placed in medium without hydrocortisone for 24 h prior to treatment with the glucocorticoid. Cells were then treated with $10^{-7}$ M budesonide or appropriately diluted vehicle control for 24 h prior to viral infection. Budesonide was again included in the medium after viral infection. The concentration of budesonide used was selected because it has previously been shown to maximally inhibit TNFa-induced RANTES production from BEAS-2B cells (48). Supernatants from cells with and without budesonide were removed at various times after viral infection and stored at −70° C. for determination of IL-8 and IL-6 protein and viral content. In some experiments, Northern analysis was used to compare RNA extracted at one hour after infection from the budesonide-treated cells with that extracted from control infected cells.

Example 6

Figure 6A:
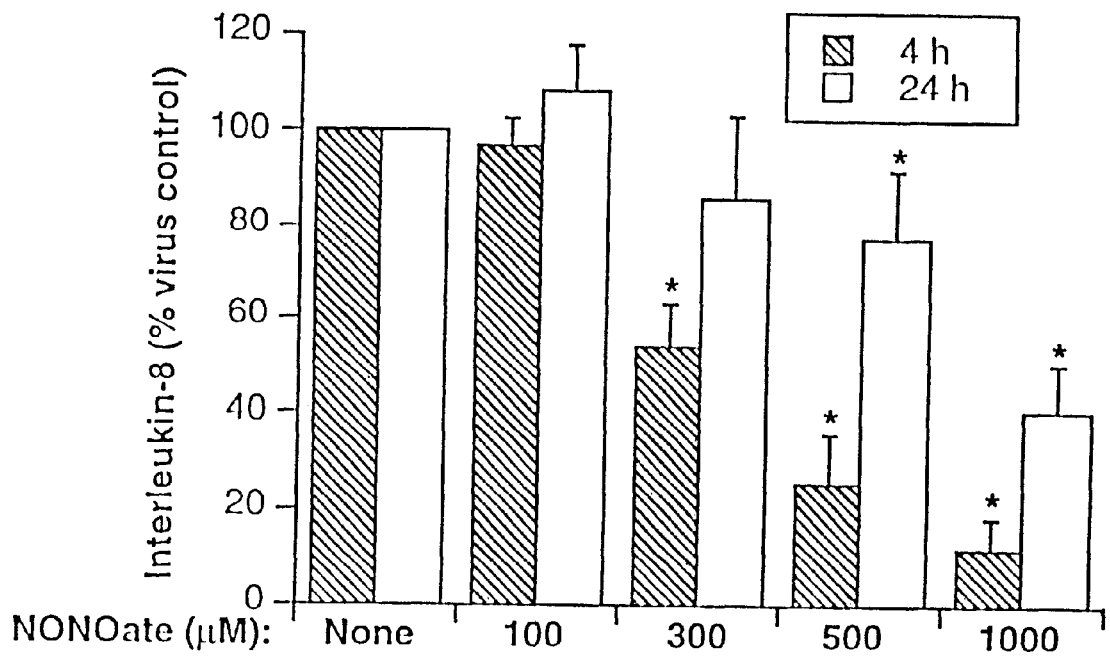
Figure 6B:
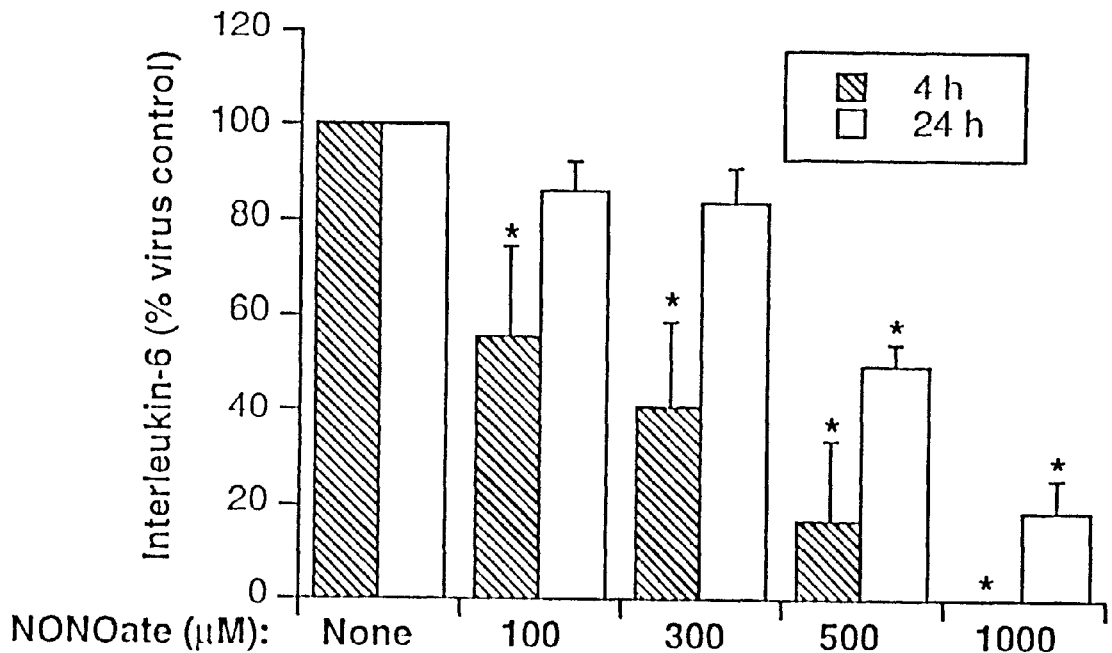
FIG. 6B shows data for IL-6 production. Asterisks indicate significant inhibition compared to levels produced at the same time after infection in the absence of NONOate ($p<0.05$ in each case).
Figure 7:
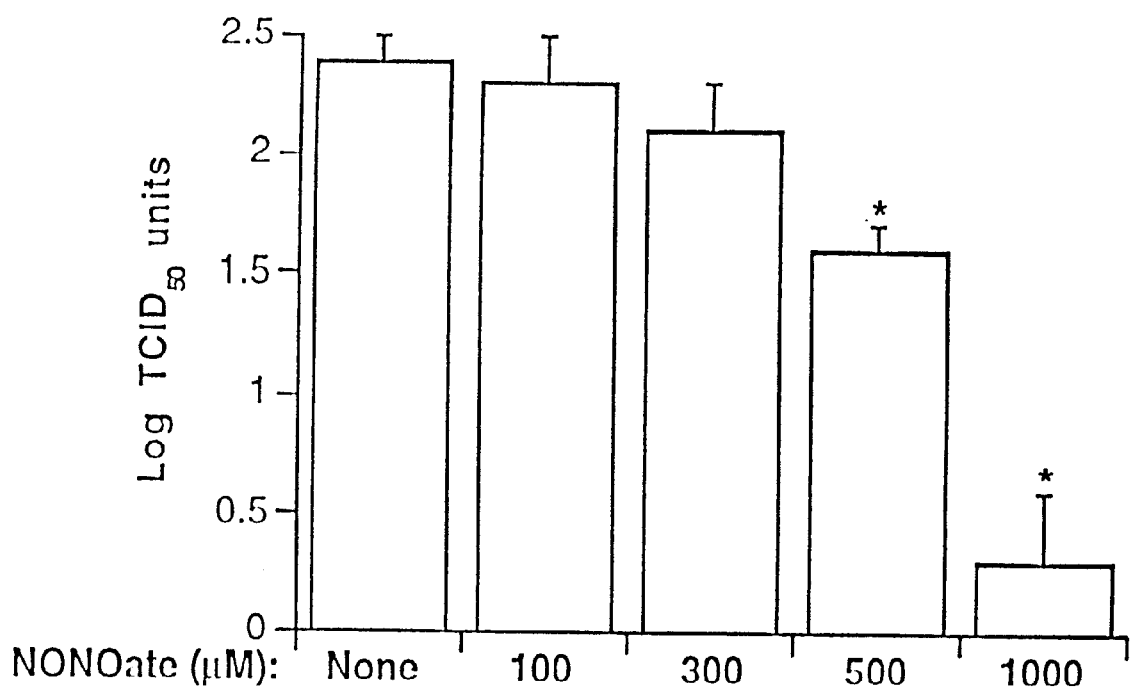
FIG. 7: Dose-dependent inhibition by NONOate of HRV-16 titers in BEAS-2B supernatant recovered 24 h after viral exposure. Data represent mean ±SEM of values from 4 experiments. Asterisks indicate significant inhibition compared to levels produced in the absence of NONOate ($p<0.05$ in each case).

Effect of a nitric oxide donor on cytokine production and viral titers: Supernatants were collected at 4 and 24 h post HRV-16 infection from BEAS-2B cells incubated in the absence or presence of NONOate and were assayed for viral content and levels of cytokines. NONOate significantly inhibited IL-8 and IL-6 production in a dose dependent manner (FIG. 6). IL-6 production was significantly inhibited by doses of NONOate as low as 100 μM. The levels of cytokine generated were inhibited more at 4 h than 24 h, presumably due to the waning levels of NO at 24 h. Viral titers were also significantly inhibited by NONOate (FIG. 7). Viral content in the supernatant collected at 24 h was almost completely eliminated by 1000 μM NONOate. Supernatants from a second 24 h collection, however, contained similar amounts of virus whether the cells had been treated with NONOate or not (Table 2). In parallel studies, the effects of NONOate on epithelial cell viability and cell numbers were assessed. There was no significant effect of NONOate on cell viability at any dose or time. There was a small, but significant, decrease in cell number with 1000 μM NONOate at 24 h only (1.7±0.4×10$^6$ cells/well without NONOate versus 1.2±0.4×10$^6$ cells/well with NONOate, n=3, P<0.05). No such effects were observed at lower NONOate doses. The effects of NONate were also confirmed using purified HRV 16 (not shown).

The inhibitory effects of NONOate were not limited to HRV-16 infection. Cytokines produced from BEAS-2B cells infected with another major strain, HRV-14 , or a minor strain, HRV-1A, were also significantly inhibited by NONOate. In the presence of 500 μM NONOate, virus-induced IL-8 production in BEAS-2B cells was inhibited by about 60% at 4 h (350±51 to 117±59 pg/ml for HRV-14 and 1857±58 to 670 64 pg/ml for HRV-1A, n=3,p<0.01). In addition, NONOate inhibited viral titers in supernatants collected from BEAS-2B cells 24 h post HRV-14 infection (data not shown). The capacity of NONOate to inhibit rhinovirus-induced cytokine production was also observed in primary human cells. In one experiment, 1000 μM NONOate reduced virally-induced levels of IL-8 , measured 4 h after infection, from 1400 pg/ml to 366 pg/mi, while, in a second experiment, IL-8 was reduced from levels of 3420 pg/ml in virally-infected cells to 1980 pg/ml and 1030 pg/ml in cells treated with 500 μM and 1000 μM NONOate, respectively.

Figure 8A:
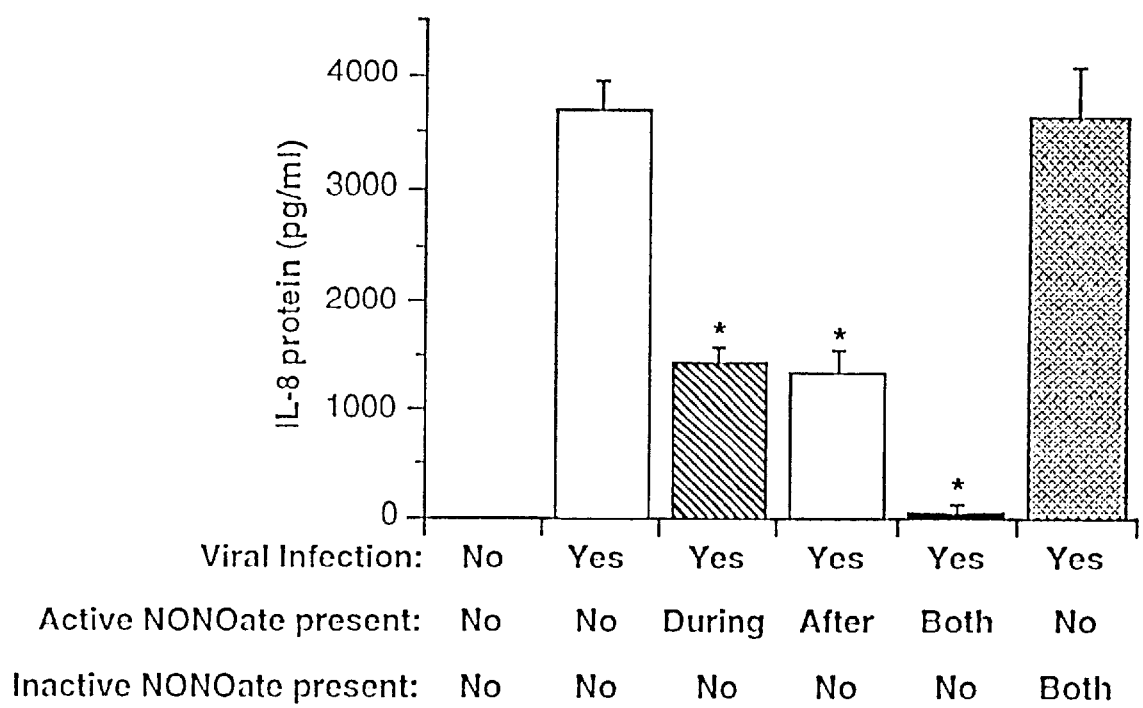
FIG. 8A shows mean ±SEM of values for IL-8 production from 3 experiments.
Figure 8B:
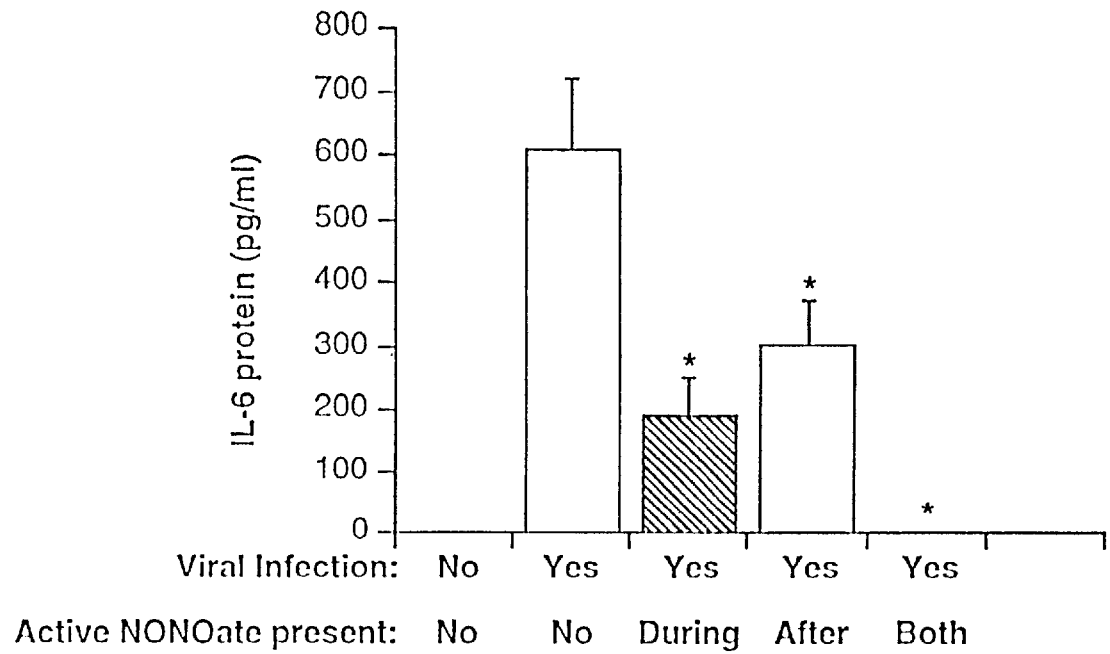
FIG. 8B shows data for IL-6. Asterisks indicate significant inhibition compared to levels produced by virus alone ($p<0.05$ in each case).
Figure 9A:
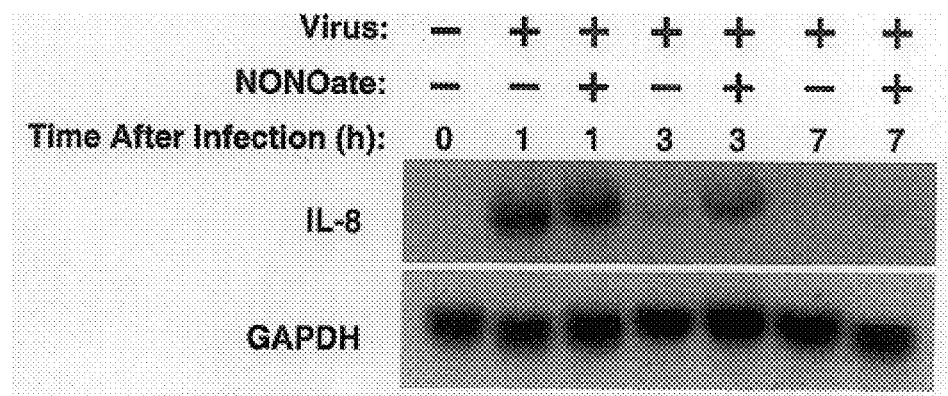
FIGS. 9A and 9B show representative Northern blots for each cytokine and for the housekeeping gene, GAPDH FIGS. 9C and 9D show the mean ±SEM values of densitometric ratios for 3 experiments.
Figure 9C:
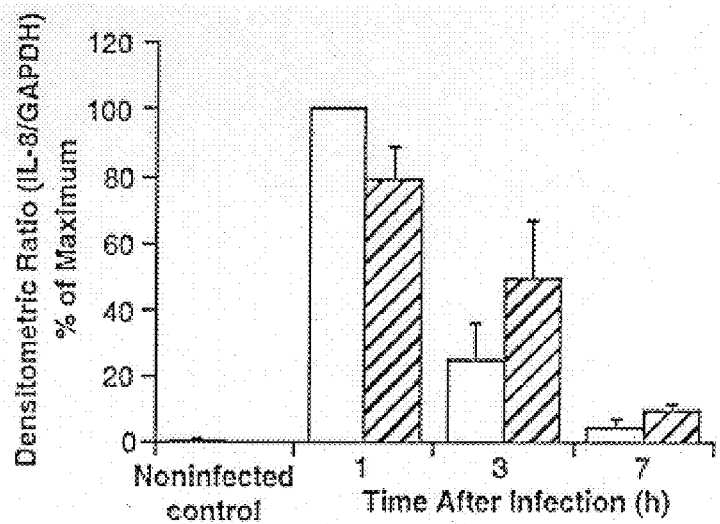
FIG. 9: Effects of NONOate (500 $\mu$M on steady state mRNA levels and protein for IL-8 (Left) and IL-6 (Right) at differing times after infection with HRV-16.
FIGS. 9E and 9F show the mean ±SEM values of protein produced for 3 experiments at each time point. Asterisks indicate significant inhibition by NONOate compared to levels produced by virus alone ($p<0.05$ in each case).
Figure 9E:
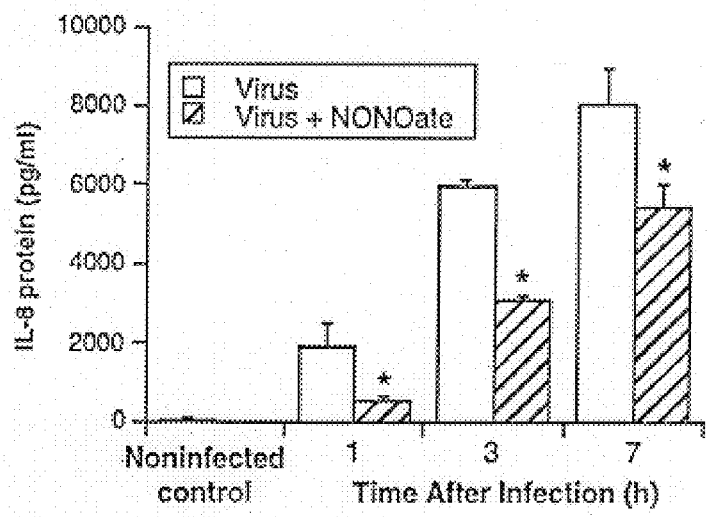
Figure 9B:
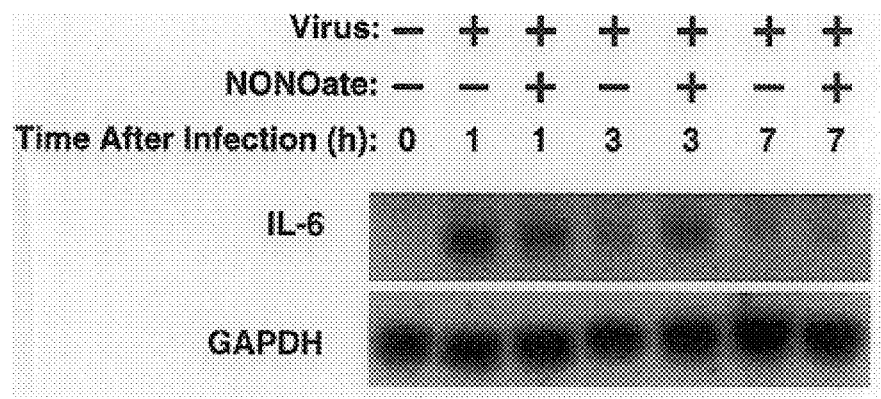
Figure 9D:
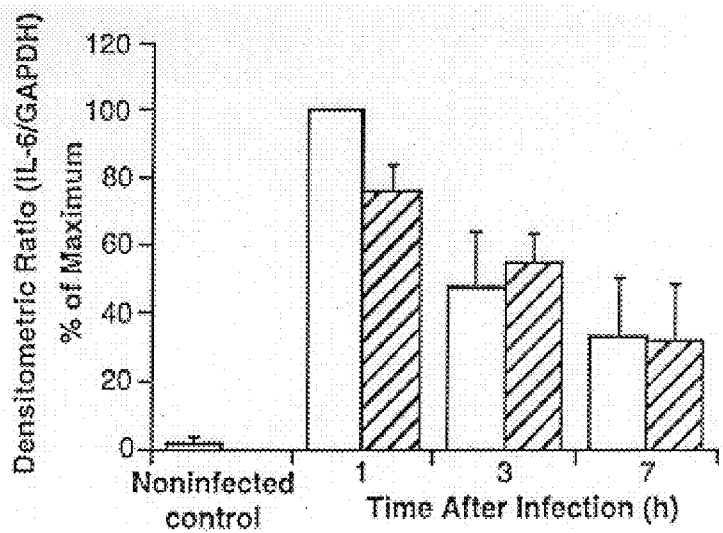
Figure 9F:
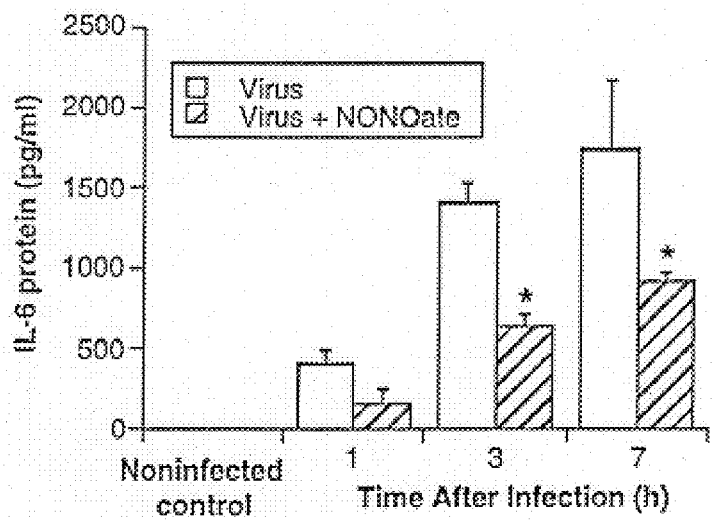

To further examine NONOate effects, additional experiments were conducted in which NONOate was added only during or after viral infection. FIG. 8 demonstrates that NONOate present only during virus exposure, or only following virus infection, inhibited IL-8 and IL-6 production by 50–60%. Complete inhibition of protein production was observed if NONOate was present both during and after viral exposure.

To determine if the observed inhibition was specifically due to nitric oxide, experiments were conducted with active NONOate and with NONOate that had released all the available NO. FIG. 8 shows that the inactive compound did not inhibit IL-8 production.

Effect of NONOate on cytokine production and viral replication: NONOate was prepared in alkaline solution (0.01 M NaOH) as a 100 mM stock solution, which was kept at 4° C. until use. New stock solutions of NONOate were prepared for each experiment and used within 1 h of preparation. The defined half-life of NO release from NONOate is 76 min at pH 7.4 and 22° C. (Cayman Chemical Co., Ann Arbor, Mich.). Under alkaline conditions, the NONOate does not release nitric oxide. Aliquots of the alkaline stock solution were added directly to the BEAS-2B culture medium (pH 7.4) in a final concentration range of 100 $\mu$M to 1000 $\mu$M. For most experiments, the NONOate was present both during and following the virus exposure. In some experiments, the NONOate was added only during the exposure to virus or only after the exposure to virus. Supernatants from BEAS-2B cells incubated with or without NONOate were removed at various times after viral infection and stored at −70° C. for later determination of IL-8 and IL-6 protein and viral content. In some cases, RNA extracted at various times after infection from the NONOate-treated cells and from control infected cells were compared by Northern analysis. To control for nonspecific effects of the NONOate compound, experiments were performed in which cells were treated with an inactive solution of NONOate. Inactivation was accomplished by placing a 1000 $\mu$M solution of NONOate in medium at pH 7.4 at room temperature for 24 h to allow the NONOate to release all of the available NO prior to adding it to the cell cultures.

Kinetics and mechanisms of the NONOate inhibition of IL-6 and IL-8 production: To examine the time course of NONOate inhibition, BEAS-2B cells were studied in the presence and absence 500 $\mu$M NONOate at various times after HRV 16 infection. The inhibitory effect of NONOate was most pronounced at the earliest time points with a 60–70% reduction in protein levels at 1 h, 50% at 3 h, and 30–40% at 7 h (FIG. 9). These results probably reflect the declining concentration of nitric oxide in the medium as the NONOate degraded. Interestingly, the NONOate did not alter levels of cytokine mRNA expression. As shown in FIG. 9, mRNA levels for BEAS-2B cells infected with HRV 16 in the presence or absence of NONOate were not significantly different. There was a tendency for the 3 and 7 h IL-8 mRNA to be higher in the NONOate treated cells. In additional control studies, NONOate alone had no effect on mRNA expression for IL-8 or IL-6 nor did inactive NONOate alter virally-induced expression of mRNA for IL-8 or IL-6 in BEAS-2B cells (data not shown). Probes for Northern Blotting: A full length cDNA for IL-8 was obtained by reverse transcription-polymerase chain reaction (RT-PCR) using RNA extracted from the human BEAS-2B cell line. The full length cDNA was cloned into a pCR II vector (Invitrogen Corp., San Diego, Calif.) between two EcoR1 sites and grown in competent *E. Coli* XL1-Blue cells (Stratagene, LaJolla, Calif.). The sequence of the cDNA probe used for Northern analysis was identical to the published sequence of IL-8 (31, 34) by di-deoxy sequencing. A full length cDNA for IL-6 was kindly provided by Dr. Steven Gillis (Immunex, Seattle, Wash.). The full length cDNA for glyceraldehyde 3-phosphate dehydrogenase (GAPDH) was purchased from Clontech Palo Alto, Calf.). Probes for IL-8, IL-6, and GAP were labeled to a high specific activity by the random primer method (15) using $a^{32}P$ dCTP and a Random Primer DNA Labeling Kit (Boehringer Mannheim Indianapolis, Ind.). Unincorporated nucleotides were separated using Nuctrap Push Columns (Stratagene).

RNA Extraction and Northern Analysis: Total cellular RNA was extracted from BEAS-2B cells using RNAzol B (1 ml/10 cm$^2$) in a modification of the method of Chomczynski and Sacchi (9). Briefly, cell monolayers were lysed with RNAzol B and transferred to a 13 ml polypropylene tube to which chloroform (0.1 ml/1 ml RNAzol) was added. A chilling on ice for 5 min, the samples were centrifuged at 7900×g for 30 min at 4° C. The aqueous phase was precipitated with an equal volume of ice-cold 95% ethanol at −20° C. overnight. After repeat centrifugation, the RNA pellet was washed twice in 75% ethanol, dried and dissolved in 50 $\mu$l of 0.2% diethylpyrocarbonate-treated water. The integrity of each RNA was assessed by electrophoresis of an aliquot (0.5 $\mu$g) on a 1% agarose gel with 0.5 $\mu$g ethidium bromide/ml buffer. RNA was stored at −80° C.

For Northern analysis, equal amounts (15–20 $\mu$g) of RNA from each experimental condition were electrophoresed on a 1% agarose/2.2 M formaldehyde gel in a Mops buffer system. The RNA was transferred to a nylon membrane (GeneScreen Plus, New England Nuclear Research Products, Wilmington, Del.). The membranes were crossed by exposure to ultraviolet light and then prehybridized in 10 mls of buffer containing 4.5 ml formamide, 2.5 ml 10×Denhardt's, 2 ml 20×SSPE, 1 ml 20% SDS, and 100 $\mu$g denatured salmon sperm DNA/ml in a hybridization oven for 2 hours at 42° C. Immediately following the prehybridization, the appropriate $a^{32}P$-labeled cDNA probe was added to the prehybridization solution and the mixture was rotated for an additional 18 h at 42° C. The blots were washed to a final stringency of 0.2×SSC/0.2% SDS at 60° C. and exposed to film (Biomax Miss., Kodak, New Haven, Conn.) using two Lightening Plus Screens at −70° C. Films were routinely developed for varying times to ensure that band intensities assessed by densitometry were within the linear range for the film. Densitometry was performed using a scanning densitometer (UVP gel documentation system, San Gabriel, Calif.) and densitometric analysis was performed using NIH Image software.

Example 7

This example demonstrates the affect of NONOate on eosinophil-active cytokines in rhinoviral infection Since increased eosinophilia in the lower airways plays an important role in asthma, we have examined the effects of NONOate on virally induced production of cytokines that effect eosinophil function. These cytokines include granulocyte macrophage-colony stimulating factor (GM-CSF), which promotes the survival and enhances the activation of eosinophils, and RANTES, which is a potent chemotactic factor for eosinophils, memory T lymphocytes, monocytes, and basophils. FIG. 10 shows the protein levels for GM-CSF and RANTES produced by epithelial cells in the presence and absence of NONOate, 24 hours following rhinovirus (HRV-16) infection. Addition of NONOate significantly inhibited the viral induction of both cytokines, suggesting that nitric oxide may play a significant role in regulating the production of eosinophil-activating cytokines, during virally induced asthma attacks.

Figure 11:
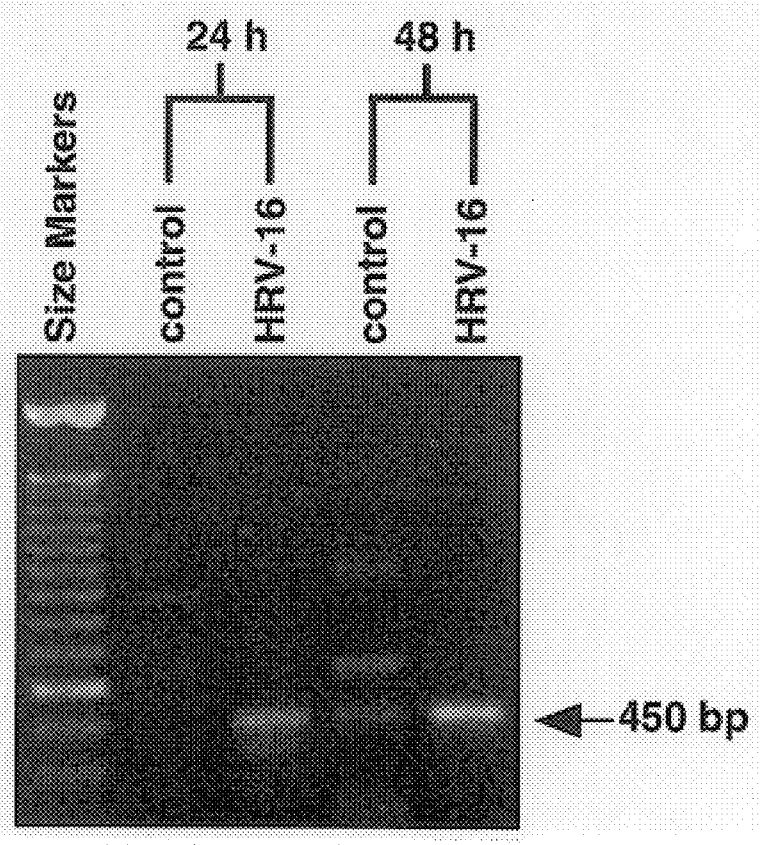
FIG. 11. HRV infection of cultured primary human bronchial epithelial cells induces expression of mRNA for iNOS. Cells were exposed to medium alone (lanes 2 and 4) or to HRV-16 (lanes 3 and 5). Total cellular RNA was extracted and subjected to RT-PCER for iNOS at 24 hours (lanes 2 and 3) and 48 hours (lanes 4 and 5). The primers used for this PCR amplify a product of 500 bp. Lane 1 contains the DNA ladder to indicate molecular size.

We have hypothesized that nitric oxide is an important part of the host antiviral response to rhinoviruses. In recent studies, we have examined whether rhinovirus infection of epithelial cells alters gene expression of inducible nitric oxide synthase (iNOS), the enzyme that produces nitric oxide. Using RT-PCR, we have assessed gene expression of iNOS in RNA isolated from non-infected and HRV-16 infected primary human bronchial epithelial cells at 24 and 48 hours. As shown in FIG. 11, viral infection induced the expression of mRNA for iNOS at both 24 and 48 hours after viral infection. These data support the concept that iNOS gene expression is induced as part of the host response to viral infection.

We have previously demonstrated that HRV-14 induces the production of IL-8 and IL-6 from BEAS-2B cells (49), and now show that other major group strains (HRV-16 and HRV-39), and type 1A of the minor group all share this ability, suggesting that the induction of proinflammatory cytokines may occur with many, if not all, rhinoviruses. We have ready shown that cytokine production by HRV-14 can be blocked both by antibodies to ICAM-1 and by UV inactivation of the virus (49). Our current studies not only showed that the effects of HRV-16 can be abrogated by UV inactivation, but also that a purified preparation of HRV-16 induced cytokine production. Taken together, these data indicate that cytokine induction is specifically due to virus, and not to some contaminant of the viral stock solutions. Moreover, the common nature of this response implies that the induction of epithelial cell cytokine production may play an important role in the pathogenesis of upper respiratory viral infections in humans, a concept that is supported further by the the fact that other viruses, such as influenza and respiratory syncytial virus (RSV) also induce epithelial cytokine production before they cause overt cytotoxicity (2, 8, 33, 38).

The significance of the differences in levels of cytokine production by each strain are difficult to interpret because the titer of viral strains are determined in several different cell lines and may not be exactly comparable. It is clear, however, that the kinetics of cytokine mRNA expression and protein secretion varied between strains of rhinovirus. Infection with HRV-14 led to a time-dependent accumulation of mRNA for IL-8 and IL-6, with observed levels being maximal at 3 h post infection and remanding elevated at 24 h after infection. Consistent with our earlier report (49), production of protein for each cytokine increased up to 24 h post infection but production during a second 24 h period was not different from control, noninfected cells (not shown). This time course of protein production was similar to that observed with this viral strain in A549 type II epithelial cells (55), although the time course for mRNA accumulation differs somewhat, presumably reflecting differences of the two cell populations. Interestingly, the time course of mRNA expression and cytokine production were more rapid, and the magnitude of the response was greater, for cells infected with HRV-16 than with HRV-14 . Not only were mammal mRNA and protein levels achieved more quickly, but they were more transient in nature, being essentially complete within 7 h. As for HRV 14, cytokine production during a second 24 h period after infection with HRV 16 was not different from control, noninfected cells (not shown), The reasons for the difference in initial rates of IL-8 and IL-6 production by HRV 14 and HRV 16 are unknown but could relate to a difference in recognition, uptake or uncoating of the two viral strains in BEAS-2B cells. Despite the different rates of cytokine production, no differences in the rates of viral replication were observed between the 2 strains. In each case, virus was detected in the supernatants of BEAS-2B cells by 7 hours after infection and reached maximal levels by 24 hours. A second 24 hour collection, produced similar titers to the first 24 hour sample, suggesting that viral proliferation and release into the culture medium were occurring at a constant rate. The transient induction of IL-8 and IL-6 by both viral strains in the setting of continued viral replication suggests that an early event in the viral infection, and not viral replication itself stimulates the production of proinflammatory cytokines. This rapid production of cytokines raises the speculation that this relatively early event in the pathogenesis of colds may be important to initiate rapid inflammatory cell infiltration.

To further elucidate the biochemical mechanisms of virus-induced cytokine generation, we examined the effects of selected drugs on virus-induced expression of mRNA and protein for cytokines. The protein synthesis inhibitor, cycloheximide, did not alter levels of mRNA for IL-8 or IL-6, suggesting that de novo synthesis of proteins were not required for rhinovirus-induced mRNA expression. This is consistent with the recent observations in A549 cells, indicating that induction of IL-6 by HRV-14 occurs via a nuclear factor kB-dependent pathway that is unaffected by cycloheximide (55).

Glucocorticosteroids have been shown to inhibit the production of several cytokines in patients with allergic inflammatory diseases (46, 52), as well as in cell culture systems (45, 48). We evaluated, for the first time, the effects of a potent glucocorticoid on viral replication and on induced IL-8 and IL-6 mRNA expression and protein production in rhinovirus infected epithelial cells. Budesonide had no effect on mRNA expression for either cytokine but caused a modest inhibition of secreted protein levels. This reduction in protein secretion in the absence of changes in mRNA levels could reflect an ability of glucocorticoids to alter post-transcriptional events involved in cytokine protein production or secretion. It has previously been reported that glucocorticoids, at best, modestly inhibit IL-8 mRNA and protein production from cultured epithelial cells exposed to cytokines (27, 30), but dexamethasone has been reported to inhibit $TNF_a$-induced IL-6 mRNA and protein production from BEAS-2B cells (30). The lack of effect of budesonide on viral titers, and the modest inhibition of IL8 and IL-6 secretion, are consistent, however, with in vivo studies of experimental rhinovirus infections in which glucocorticoids had little or no effect on viral shedding and symptoms (14, 17).

It is now clear that NO can exert a broad range of actions, serving as a vasodilator, neurotransmitter, antimicrobial and immune regulator (39). In recent years, NO has also been shown to have antiviral properties in murine cell lines and in an in vivo mouse model. Replication of several viruses, including vaccinia virus (20), herpes simplex-1 (12, 24), vesicular stomatitis virus (7), Coxsackie virus (32), and poliovirus (26) was inhibited by induction of NO synthase, the enzyme that generates NO, or by the addition of the NO donor, S-nitroso-1-acetyl penicillanine. Given that levels of NO are increased in exhaled air from human subjects with upper respiratory viral infections (25), we examined whether NO could inhibit rhinovirus replication, and extended these studies to evaluate the effects of NO on rhinovirus-induced production of IL-6 and IL-8. Although normal human respiratory epithelial cells have been shown to express both the constitutive and inducible forms of NO synthase (4), the expression of these enzymes is markedly reduced in the BEAS-2B cell line (data not shown). For this reason, and to ensure a controlled level of NO exposure, we used NONOate, a donor that releases NO with a defined half-life. Our data show, for the first time, that NO can inhibit both rhinovirus replication and rhinovir induced production of IL-8 and IL-6 in human respiratory epithelial cells. These effects were dose-dependent and occurred in the absence of any effects on epithelial cell viability. Inhibition of cytokine production was more pronounced at 4 hours after infection than at 24 hours post infection, while viral shedding from epithelial cells also recovered to normal levels during a second 24 h collection period. These data are consistent with the ability of NONOate to cause inhibition only when able to release significant amounts of NO, and indicate that both viral replication and cytokine production resume as the compound degrades. Further support for the key role of NO release is provided by our data that inactivated NONOate had no effects on viral titer or cytokine production.

The ability of NONOate to cause partial inhibition of cytokine production even when present only after the viral infection period suggests that NONOate is not inhibiting by directly killing the virus, or by inhibiting the virus from entering the BEAS-2B cells. This is also supported by the ability of viral titers to recover after NONOate degradation. Rather, it seems likely that NO is inhibiting one or more early events in the viral infection process. The failure of NONOate to inhibit cytokine mRNA expression at any time point examined suggests that NO may be functioning by a post-transcriptional mechanism, but further studies are necessary to confirm this. Precedent exists, however, for the capacity of NO to inhibit protein synthesis in other cell types (13, 23).

In summary, we have demonstrated that multiple strains of rhinoviruses induce production of proinflammatory cytokines from human respiratory epithelial cells but that there are variations in terms of the levels and kinetics of cytokine production by different strains. Although glucocorticoids modestly inhibit cytokine secretion induced by rhinovirus-infection they do not alter cytokine mRNA expression or viral replication. In contrast, NO markedly inhibits rhinovirus replication and virally induced cytokine expression, without affecting mRNA levels for these cytokines. Although further studies are necessary to elucidate the mechanisms by which NO inhibits viral replication and cytokine production, our data indicate that topical application of NO donors may provide a novel therapeutic approach for the treatment of rhinovirus induced colds and their complications.

REFERENCES

1. Akiro, S., T. Hirano, T. Taga, and T. Kishimoto. 1990. Biology of multifunctional cytokines: IL 6 and related molecules (IL 1 and TNF). FASEB J. 4:2860–2867.
2. Arnold, R, B. Humbert, H. Werchau, H. Gallati, and W. K önig. 1994. Interleukin-8, interleukin-6, and soluble tumour necrosis factor receptor type I release from a human pulmonary epithelial cell line (A549) exposed to respiratory syncytial virus. Immunology. 82:126–133.
3. Arola, M, T. Ziegler, H. Puhakka, O. P. Lehtonen, and O. Ruuskanen. 1990. Rhinovirus in otitis media with effusion Ann. Otol. Rhinol. & Laryngol. 99:451–453.
4. Asano, K, C. B. E. Chee, B. Gaston, C. M. Lilly, C. Gerard, J. M. Drazen, and J. S. Stamler. 1994. Constitutive and inducible nitric oxide synthase gene expression, regulation, and activity in human lung epithelial cells. Proc. Natl. Acad. Sci. USA 91:10089–10093.
5. Baggiolini, M., A. Walz, and S. L. Kunkel. 1989. Neutrophil-activating peptide-1/Interleukin 8, a novel cytokine that activates neutrophils. J. Clin. Invest. 84:1045–1049.
6. Bardin, P. G., S. L. Johnston, G. Sanderson, S. Robinson, M. A. Pickett, D. J. Fraenkel, and S. T. Holgate. 1994. Detection of rhinovirus infection of the nasal mucosa by oligonucleotide in situ hybridization. Am. J. Respir. Cell Mol. Biol. 10:207–213.
7. Bi, Z., and C. S. Reiss. 1995. Inhibition of vesicular stomatitis virus infection by nitric oxide. J. Virol. 69:2208–2213.
8. Choi, A. M. K, and D. B. Jacoby. 1992. Influenza virus A infection induces Interleukin-8 gene expression in human airway epithelial cells. FEBS Lett. 309:327-329.
9. Chomczynski, P., and N. Sacchi 1987. Single-step method of RNA isolation by acid guanidinium thiocyanate-phenolchloroform extraction. Anal. Biochem. 162:156–159.
10. Churchill, L., F. H. Chilton, J. H. Resau, R. Bascom, W. C Hubbard, and D. Proud. 1989. Cyclooxygenase metabolism of endogenous arachidonic acid by cultured human tracheal epithelial cells. Am. Rev. Respir. Dis. 140:449–459.
11. Couch, R. B. 1996. Rhinoviruses, pp. 713–734. In B. N. Fields and D. M. Knipe and P. M. Howley (ed.), Fields Virology, 3rd. edition. Lippincott-Raven, Philadelphia.
12. Croen, K. D. 1993. Evidence for an antiviral effect of nitric oxide. Inhibition of herpes simplex virus type 1 replication. J. Clin. Invest. 91:2446–2452.
13. Curran, R. D., F. K Ferrari, P. H. Kispert, J. Stadler, D. J. Stuehr, R. L. Simmons, and T. R. Billiar. 1991. Nitric oxide and nitric oxide-generating compounds inhibit hepatocyte protein synthesis. FASEB J. 5:2085–2092.
14. Farr, B. M., J. M. Gwaltney, Jr., J. O. Hendley, F. G. Hayden, R. M. Naclerio, T. McBride, W. J. Doyle, J. V. Sorrentino, D. K Riker, and D. Proud. 1990. A randomized controlled trial of glucocorticoid prophylaxis against experimental rhinovirus infection J. Infect. Dis. 162:1173–1177.
15. Feinberg, A. P., and B. Vogelstein. 1983. A technique for radiolabelling DNA restriction endonuclease fragments to high specific activity. Anal. Biochem. 132:6–13.
16. Gern, J. E., R. Vrtis, E. A. B. Kelly, E. C. Dick, and W. W. Busse. 1996. Rhinovirus produces nonspecific activation of lymphocytes through a monocyte-dependent mechanism. J. Immunol. 157:1605–1612.
17. Gustafson, L. M., D. Proud, J. O. Rendley, F. G. Hayden, and J. M. Gwaltney, Jr. 1996. Oral prednisone therapy in experimental rhinovirus infections. J. Allergy Clin. Immunol. 97:1009–1014.
18. Gwaltney, J. M., J. O. Hendley, G. Simon, and W. S. Jordan. 1966. Rhinovirus infections in an industrial population. I. The occurrence of illness. N. Engl. J. Med. 275:1261–1268.
19. Gwaltney, J. M, Jr., C. D. Philips, R. D. Miller, and D. K Riker. 1994. Computed tomographic study of the common cold. N. Engl. J. Med. 330:25–30.
20. Harris, N., R. M. L Buller, and G. Karupiah. 1995. Gamma interferon-induced, nitric oxide-mediated inhibition of vaccinia virus replication. J. Virol. 69:910–915.
21. Johnston, S. L, P. K. Pattemore, G. Sanderson, S. Smith, M. J. Campbell, L. K. Josephs, A. Cunningham, B. S. Robinson, S. H. Myint, M. E. Ward, D. A. J. Tyrrell, and S. T. Holgate. 1996. The relatioship between upper respiratory infections and hospital admissions for asthma: a time-trend analysis. Am. J. Respir. Crit. Care Med. 154:654–660.
22. Johnston, S. L., P. K Pattemore, G. Sanderson, S. Smith, F. Lampe, L. Josephs, P. Sympington, S. O'Toole, S. H. Myint, D. A. Tyrrell, and S. T. Holgate. 1995. Community study of role of viral infections in exacerbations of asthma in 9–11 year old children. Br. Med. J. 310:1225–1228.
23. Karupiah, G., and N. Harris. 1995. Inhibition of viral replication by nitric oxide and its reversal by ferrous sulfite and tricarboxylic acid cycle metabolites. J. Exp. Med. 181:2171–2179.
24. Karupiah, G., Q.-w. Xie, R. M. L. Buller, C. Nathan, C. Duarte, and J. D. MacMicking. 1994. Inhibition of viral replication by interferon-g-induced nitric oxide synthase. Science. 261:1445–1448.
25. Kharitonov, S. A., D. Yates, and P. J. Barnes. 1995. Increased nitric oxide in exhaled air of normal human subjects with upper respiratory tract infections. Eur. Respir. J. 8:295–297.
26. Komatsu, T., Z. Bi, and C. S. Reiss. 1996. Interferon-g induced type I nitric oxide synthase activity inhibits viral replication in neurons. J. Neuroimmunol. 68:101–108.

27. Kwon, O. J., B. T. Au, P. D. Collins, J. N. Baraniuk, L. M. Adcock, K F. Chung, and P. J. Barnes. 1994. Inhibition of interleukin-8 by dexamethasone in human cultured airway epithelial cells. Immunology. 81:389–394.
28. Larsen, C. G., A. O. Anderson, E. Appella, J. J. Oppenheim, and K. Matsushima. 1989. The neutrophil activating protein (NAP-1) is also chemotactic for T lymphocytes. Science. 243:1464–1466.
29. Levandowski, R. A., C. W. Weaver, and G. G. Jackson. 1988. Nasal secretion leukocyte populations determined by flow cytometry during acute rhinovirus infection. J. Med. Virol. 25:423–432.
30. Levine, S. J., P. Larivée, C. Logun, C. W. Angus, and J. H. Shelhamer. 1993. Corticosteroids differentially regulate secretion of IL-6, IL-8, and G-CSF by a human epithelial cell line. Am. J. Physiol. 265:L360–L368.
31. Lindley, I., H. Aschauer, J. M. Seifert, C. Lam, W. Brunowsky, E. Kownatski, M. Thelen, P. Peveri, B. Dewald, V. von Tscharner, A. Walz, and M. Baggiolini 1988. Synthesis and expression in escherichia coli of the gene encoding monocyte-derived neutrophil-activating factor: biological equivalence between natural and recombinant neutrophil-activating factor. Proc. Natl. Acad. Sci. USA 85:9199–9203.
32. Lowenstein, C. J., S. L Hill, A. Lafond-Walker, J. Wu, G. Allen, M. Landavere, N. R. Rose, and A. Herskowitz. 1996. Nitric oxide inhibits viral replication in murine myocarditis. J. Clin. Invest. 97:1837–1843.
33. Matsukura, S., F. Kokubo, H. Noda, H. Tokunaga, and M. Adachi. 1996. Expression of IL-6, IL-8, and RANTES on human bronchial epithelial cells, NCI-H292, induced by influenza virus A. J. Allergy Clin. Immunol. 98:1080–1087.
34. Matsushima, K., K Morishita, T. Yoshimura, S. Lavu, Y. Kobayashi, W. Lew, E. Appella, H. F. Kung, E. J. Leonard, and J. J. Oppenheim. 1988. Molecular cloning of a human monocyte-derived neutrophil chemotactic factor (MDNCF) and the induction of MDNCF by interleukin 1 and tumor necrosis factor. J. Exp. Med. 167:1883–1893.
35. McHardy, V. U., J. M. Inglis, M. A. Calder, J. W. Crofton, I. Gregg, D. A. Ryland, P. Taylor, M. Chadwick, D. Coombs, and R. W. Riddell. 1980. A study of infective and other factors in exacerbations of chronic bronchitis. Br. J. Dis. Chest. 74:228–238.
36. Naclerio, R. M., D. Proud, L. M. Lichtenstein, A. Kagey-Sobotka, J. O. Rendley, J. Sorrentino, and J. M. Gwaltney. 1988. Kinins are generated during experimental rhinovirus colds. J. Infect. Dis. 157:133–142.
37. Nicholson, K G., J. Kent, and D. C. Ireland. 1993. Respiratory viruses and exacerbations of asthma in adults. Br. Med. J. 307:982–986.
38. Noah, T. L, and S. Becker. 1993. Respiratory syncytial virus-induced cytokine production by a human bronchial epithelial cell line. Am. J. Physiol. 265:L472–LA478.
39. Nussler, A. K, and T. R. Billiar. 1993. Inflammation, immunoregulation, and inducible nitric oxide synthase. J. Leukocyte Biol. 54:171–178.
40. Proud, D., J. M. Gwaltney, Jr., J. O. Hendley, C. A. Dinarello, S. Gills, and R. P. Schleimer. 1994. Increased levels of Interleukin-1 are detected in nasal secretions of volunteers during experimental rhinovirus colds. J. Infect. Dis. 169:1007–1013.
41. Proud, D., R. M. Naclerio, J. M. Gwaltney, and J. O. Hendley. 1990. Kinins are generated in nasal secretions during natural rhinovirus colds. J. Infect. Dis. 161:120–123.
42. Ramsay, A. J., A. J. Husband, I. A. Ramshaw, S. Bao, K. I. Matthaei, G. Koehler, and M. Kopf. 1994. The role of interleukin-6 in mucosal IgA antibody responses in vivo. Science. 264:561–563.
43. Reddel, R. R., Y. Ke, B. L. Gerwin, M. G. McMenamin, J. F. Lechner, R. T. Su, D. E. Brash, J.-B. Park, J. S. Rhim, and C. C. Harris. 1988. Transformation of human bronchial epithelial cells by infection with SV40 or adenovirus-12 SV40 hybrid virus, or transfection via strontium phosphate coprecipitation with a plasmid containing SV40 early region genes. Cancer Res. 48:1904–1909.
44. Schleimer, R. P. 1993. Glucocorticosteroids: their mechanism of action and use in allergic diseases, p. pp. 893–925. In E. Middleton and C. E. Reed and E. F. Ellis and N. F. Adkinson, Jr. and J. W. Yunginger and W. W. Busse (ed.), Allergy: Principles and Practice, 4th. ed. Mosby, St. Loius.
45. Schwiebert, L. A., L A. Beck, C. Stellato, C. A. Bickel, B. S. Bochner, and R. P. Schleimer. 1996. Glucocorticosteroid inhibition of cytokine production; relevance to antiallergic actions. J. Allergy Clin. Immunol 97:143–152.
46. Sim, T. C., L. M. Reece, K. A. Hilsmeier, J. A. Grant, and R. Alam. 1995. Secretion of chemokines and other cytokines in allergen-induced nasal responses: inhibition by topical steroid treatment. Am. J. Respir. Crit. Care Med. 152:927–933.
47. Steel, R. G. D., and J. H. Torrie. 1980. Principles and Procedures of Statistics, a Biometrical Approach, 2nd ed. McGraw-Hill, New York.
48. Stellato, C., L. A. Beck, G. A. Gorgone, D. Proud, T. J. Schall, S. J. Ono, L. M. Lichtenstein, and R. P. Schleimer. 1995. Expression of the chemokine RANTES by a human bronchial epithelial cell line. Modulation by cytokines and glucocorticoids. J. Phenol. 155:410–418.
49. Subauste, M. C., D. B. Jacoby, S. M. Richards, and D. Proud. 1995. Infection of a human respiratory epithelial cell line with rhinovirus. Induction of cytokine release and modulation of susceptibility to infection by cytokine exposure. J. Clin Invest. 96:549–557.
50. Turner, B. W., W. S. Cail, J. O. Hendley, F. G. Hayden, W. J. Doyle, J. V. Sorrentino, and J. M. Gwaltney, Jr. 1992. Physiologic abnormalities of the paranasal sinuses during experimental rhinovirus colds. J. Allergy Clin. Immunol. 90:474–478.
51. Turner, R. B., J. O. Hendley, and J. M. Gwaltney, Jr. 1982. Shedding of infected epithelial cells in rhinovirus colds. J. Infect. Dis. 145:849–853.
52. Wang, J. H., C. J. Trigg, J. L Devalia, S. Jordan, and R. J. Davies. 1994. Effect of inhaled beclomethasone dipropionate on expression of proinflammatory cytokines and activated eosinophils in the bronchial epithelium of patients with mild asthma. J. Allergy Clin. Immunol. 94:1025–1034.
53. Winther, B., S. Brofeldt, B. Christensen, and N. Mygind. 1984. Light and scanning electron microscopy of nasal biopsy material from patients with naturally acquired common colds. Acta. Otolaryngol. (Stockh). 97:309–318.
54. Winther, B., B. Farr, R. B. Turner, J. O. Hendley, J. M. Gwaltney, Jr., and N. Mygind. 1984. Histopathologic examination and enumeration of polymorphonuclear leukocytes in the nasal mucosa during experimental rhinovirus colds. Acta. Otolaryngol. Suppl. (Stockh). 413:19–24.
55. Zhu, Z., W. Tang, A. Ray, Y. Wu, O. Einarsson, M. L Landry, J. M. Gwaltney, Jr., and J. A. Elias. 1996. Rhinovirus stimulation of Interleukin-6 in vivo and in vitro.

Evidence for nuclear factor kB-dependent transcriptional activation. Clin. Invest. 97:421–430.

What is claimed is:

1. A method of alleviating symptoms induced by a rhinoviral infection comprising:
   administering an effective amount of a compound to a human infected with a rhinovirus, wherein the compound releases nitric oxide (NO).
2. The method of claim 1 wherein the rhinovirus induces common colds.
3. The method of claim 1 wherein the rhinovirus induces asthma.
4. The method of claim 1 wherein the rhinovirus induces sinusitis.
5. The method of claim 1 wherein the rhinovirus induces otitis media.
6. The method of claim 1 wherein the rhinovirus induces bronchitis.
7. The method of claim 1 wherein the compound releases NO in a controlled manner.
8. The method of claim 1 wherein the compound releases NO at pathophysiological pH.
9. The method of claim 1 wherein the compound comprises a $N_2O_2^-$ moiety.
10. The method of claim 1 wherein the compound is 3-(2-hydroxy-2-nitroso-1-propylhydrazino)-1-propanamine.
11. The method of claim 1 wherein the compound is administered by nose drops.
12. The method of claim 1 wherein the compound is administered topically.
13. The method of claim 1 wherein the compound is administered by inhalant.
14. The method of claim 1 wherein the compound is administered in a spray.
15. A method of reducing cytokine production induced by a rhinovirus, comprising:
    contacting human respiratory epithelial cells which are infected by a rhinovirus with a compound which releases NO in an amount effective to inhibit cytokine production induced by the rhinovirus.
16. The method of claim 16 wherein the cytokine is a proinflammatory cytokine.
17. The method of claim 16 wherein the cytokine is interleukin-8.
18. The method of claim 16 wherein the cytokine is interleukin-6.
19. The method of claim 16 wherein the compound comprises a $N_2O_2^-$ moiety.
20. The method of claim 16 wherein the compound is 3-(2-hydroxy-2-nitroso-1-propylhydrazino)1-propanamine.
21. The method of claim 1 wherein the compound is S-nitroso-1-acetyl penicillamine.
22. The method of claim 16 wherein the compound is S-nitroso-1-acetyl penicillamine.

* * * * *

UNITED STATES PATENT AND TRADEMARK OFFICE
CERTIFICATE OF CORRECTION

PATENT NO.    : 6,277,891 B1
DATED         : August 21, 2001
INVENTOR(S)   : Scherer P. Sanders et al.

It is certified that error appears in the above-identified patent and that said Letters Patent is hereby corrected as shown below:

Column 20,
Lines 15, 17, 19, 21 and 25, delete "16" insert -- 15 --

Signed and Sealed this

Twenty-sixth Day of November, 2002

Attest:

Attesting Officer

JAMES E. ROGAN
Director of the United States Patent and Trademark Office